(12) United States Patent
Scutt et al.

(10) Patent No.: US 8,623,907 B2
(45) Date of Patent: Jan. 7, 2014

(54) HERBICIDES

(75) Inventors: James Nicholas Scutt, Bracknell (GB); Christopher John Mathews, Bracknell (GB); Michel Muehlebach, Stein (CH)

(73) Assignee: Syngenta Participations, AG, Basel (CH)

( * ) Notice: Subject to any disclaimer, the term of this patent is extended or adjusted under 35 U.S.C. 154(b) by 101 days.

(21) Appl. No.: 12/997,539

(22) PCT Filed: Jun. 4, 2009

(86) PCT No.: PCT/EP2009/056874
§ 371 (c)(1),
(2), (4) Date: Mar. 7, 2011

(87) PCT Pub. No.: WO2009/150093
PCT Pub. Date: Dec. 17, 2009

(65) Prior Publication Data
US 2011/0152095 A1 Jun. 23, 2011

(30) Foreign Application Priority Data

Jun. 11, 2008 (GB) .................................. 0810728.6

(51) Int. Cl.
*A61K 31/382* (2006.01)
*C07D 335/02* (2006.01)

(52) U.S. Cl.
USPC .......................................... 514/437; 549/27

(58) Field of Classification Search
USPC .......................................... 514/437; 549/27
See application file for complete search history.

(56) References Cited

U.S. PATENT DOCUMENTS 6,894,005 B1 5/2005 Maetzke et al.
2005/0164883 A1 7/2005 Maetzke et al.

FOREIGN PATENT DOCUMENTS

| | | |
|---|---|---|
| CN | 1514829 | 7/2004 |
| WO | 01/17972 | 3/2001 |
| WO | 01/74770 | 10/2001 |
| WO | 2004/037749 | 5/2004 |
| WO | 2006/002810 | 1/2006 |
| WO | 2006/008107 | 1/2006 |

OTHER PUBLICATIONS

King, Med. Chem. Principle and Practice (1994), pp. 206-208.*

* cited by examiner

*Primary Examiner* — Taofiq A Solola
(74) *Attorney, Agent, or Firm* — R. Kody Jones

(57) ABSTRACT

Pyrandione, thiopyrandione and cyclohexanetrione derivatives of formula (I), which are suitable for use as herbicides.

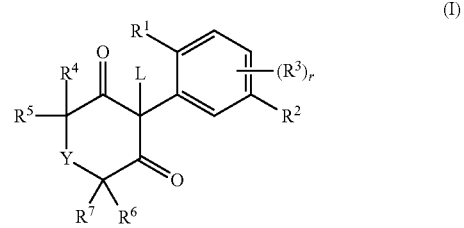

(I)

15 Claims, No Drawings

HERBICIDES

This application is a 371 of International Application No. PCT/EP2009/056874 filed Jun. 4, 2010, which claims priority to GB 0810728.6 filed Jun. 11, 2008, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting plant growth.

Cyclic diones having herbicidal action are described, for example, in WO 04/37749 and WO 01/74770.

Novel pyrandione, thiopyrandione and cyclohexanetrione compounds having herbicidal and growth-inhibiting properties have now been found.

The present invention accordingly relates to compounds of formula I

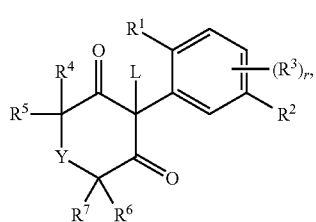

(I)

wherein $R^1$ is halogen, $C_1$-$C_4$alkyl, $C_1$-$C_4$haloalkyl, $C_3$-$C_6$cycloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, nitro or cyano;

$R^2$ is optionally substituted aryl or optionally substituted heteroaryl;

r is 0, 1, 2 or 3;

$R^3$, if r is 1, is halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylthio, $C_1$-$C_6$alkylsulfinyl, $C_1$-$C_6$alkylsulfonyl, cyano or nitro; or the substituents $R^3$, if r is 2 or 3, independently of each other, are halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylthio, $C_1$-$C_6$alkylsulfinyl, $C_1$-$C_6$alkylsulfonyl, cyano or nitro;

$R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, cyclopropyl or cyclopropyl substituted by $C_1$- or $C_2$alkyl, $C_1$- or $C_2$haloalkyl or halogen; cyclobutyl or cyclobutyl substituted by $C_1$- or $C_2$alkyl; oxetanyl or oxetanyl substituted by $C_1$- or $C_2$alkyl; $C_5$-$C_7$cycloalkyl or $C_5$-$C_7$cycloalkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl or $C_4$-$C_7$cycloalkenyl substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; cyclopropyl$C_1$-$C_5$alkyl or cyclopropyl$C_1$-$C_5$alkyl substituted by $C_1$- or $C_2$alkyl, $C_1$- or $C_2$haloalkyl or halogen; cyclobutyl$C_1$-$C_5$alkyl or cyclobutyl$C_1$-$C_5$alkyl substituted by $C_1$-$C_2$alkyl; oxetanyl$C_1$-$C_5$alkyl or oxetanyl$C_1$-$C_5$alkyl substituted by $C_1$- or $C_2$alkyl; $C_5$-$C_7$ cycloalkyl$C_1$-$C_5$alkyl or $C_5$-$C_7$cycloalkyl$C_1$-$C_5$alkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl$C_1$-$C_5$ alkyl or $C_4$-$C_7$cycloalkenyl$C_1$-$C_5$alkyl which is substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; benzyl or benzyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; or $R^4$ and $R^5$, or $R^6$ and $R^7$, are joined to form a 5-7 membered saturated or unsaturated ring in which a methylene group is optionally replaced by an oxygen or sulfur atom, or a 5-7 membered saturated or unsaturated ring substituted by $C_1$- or $C_2$alkyl, where a methylene group of the ring is optionally replaced by an oxygen or sulfur atom; or $R^4$ and $R^7$ are joined to form a 5-7 membered saturated or unsaturated ring unsubstituted or substituted by $C_1$- or $C_2$alkyl, $C_1$- or $C_2$alkoxy, $C_1$-$C_2$alkoxy$C_1$-$C_2$alkyl, hydroxy, halogen, phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl;

Y is O, C=O, $S(O)_m$ or $S(O)_nNR^8$; provided that when Y is C=O, $R^6$ and $R^7$ are different from hydrogen when either $R^4$ or $R^5$ is hydrogen, and $R^4$ and $R^5$ are different from hydrogen when either $R^6$ or $R^7$ is hydrogen;

m is 0 or 1 or 2 and n is 0 or 1;

$R^8$ is hydrogen, $C_1$-$C_6$alkyl, $C_3$-$C_6$cycloalkyl, $C_1$-$C_6$alkoxycarbonyl, tri($C_1$-$C_6$alkyl)silyl-ethyloxycarbonyl, $C_1$-$C_6$haloalkoxycarbonyl, cyano, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$cycloalkylcarbonyl, phenylcarbonyl or phenylcarbonyl substituted by $R^9$; benzylcarbonyl or benzylcarbonyl substituted by $R^9$; pyridylcarbonyl or pyridylcarbonyl substituted by $R^9$; phenoxycarbonyl or phenoxycarbonyl substituted by $R^9$; benzyloxycarbonyl or benzyloxycarbonyl substituted by $R^9$;

$R^9$ is $C_1$-$C_6$haloalkyl, $C_1$-$C_6$alkoxycarbonyl, nitro, cyano, formyl, carboxyl or halogen, and L is halogen, nitro, $C_1$-$C_6$alkylthio, thiocyanato or sulfo, and agriculturally acceptable salts thereof.

In the substituent definitions of the compounds of the formula I, the alkyl substituents and alkyl moieties of alkoxy, alkylthio etc. having 1 to 6 carbon atoms are preferably methyl, ethyl, propyl, butyl, pentyl and hexyl, in the form of their straight and branched isomers. Higher alkyl groups of up to 10 carbon atoms comprise preferably octyl, nonyl and decyl, in form of their straight and branched isomers. The alkenyl and alkynyl radicals having 2 to 6 carbon atoms as well as up to 10 carbon atoms can be straight or branched and can contain more than 1 double or triple bond. Examples are vinyl, allyl, propargyl, butenyl, butynyl, pentenyl and pentynyl. Suitable cycloalkyl and cycloalkenyl groups contain 3 or 5 to 7 and 4 to 7 carbon atoms, respectively, and are for example cyclopropyl, cyclobutyl, cyclopentyl, cyclohexyl and cycloheptyl as well as cyclopentenyl, cyclopentadienyl, cyclohexenyl and cyclohexadienyl. Cyclopropyl, cyclobutyl, cyclopentyl and cyclohexyl are preferred. A methylene group in these cycloalkyl and cycloalkenyl rings may be replaced by a heteroatom such as sulphur or oxygen, which leads to rings like tetrahydrofuranyl, dihydropyranyl, tetrahydropyranyl, dioxanyl, dioxolyl, and tetrahydrothiophenyl. Preferred halogens are fluorine, chlorine and bromine. Preferred examples of aryls are phenyl and naphthyl. Preferred examples of heteroaryls are thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl and pyridazinyl, and, where appropriate, N-oxides and salts thereof. These aryls and heteroaryls can be substituted by one or more substituents, where preferred substituents are halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

In a preferred group of compounds of the formula I, $R^1$ is halogen, $C_1$-$C_4$alkyl, $C_1$-$C_4$haloalkyl, $C_3$-$C_6$cycloalkyl, $C_2$-$C_4$alkenyl or $C_2$-$C_4$ alkynyl.

In another preferred group of compounds of the formula I, $R^2$ is aryl or heteroaryl; or aryl or heteroaryl both substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, phenoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_3$-$C_6$cycloalkyl, $C_1$-$C_4$alkylsulfonyloxy, $C_1$-$C_4$haloalkylsulfonyloxy, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, nitro, cyano, thiocyanato, hydroxy, amino, $C_1$-$C_6$alkylamino, $C_1$-$C_6$dialkylamino, $C_3$-$C_6$cycloalkylamino, morpholino, thiomorpholino, $C_1$-$C_6$alkylcarbonylamino, $C_1$-$C_6$alkoxycarbonylamino, $C_3$-$C_6$ alkenyloxycarbonylamino, $C_3$-$C_6$ alkynyloxycarbonylamino, $C_1$-$C_6$ alkylaminocarbonylamino, di($C_{1-6}$alkyl)aminocarbonylamino, formyl, $C_1$-$C_6$alkylcarbonyl, $C_2$-$C_6$alkenylcarbonyl, $C_2$-$C_6$alkynylcarbonyl, carboxy, $C_1$-$C_6$alkoxycarbonyl, $C_3$-$C_6$alkenyloxycarbonyl, $C_3$-$C_6$alkynyloxycarbonyl, carboxamido, $C_1$-$C_6$alkylaminocarbonyl, di($C_1$-$C_6$alkyl)aminocarbonyl, $C_1$-$C_6$alkylcarbonyloxy, $C_1$-$C_6$alkylaminocarbonyloxy, di($C_1$-$C_6$alkyl)aminocarbonyloxy or $C_1$-$C_6$alkylthiocarbonylamino;

Preferably, $R^2$ in the compounds of formula I is aryl or heteroaryl; or aryl or heteroaryl both substituted by halogen, $C_1$-$C_4$alkyl, $C_1$-$C_4$haloalkyl, phenoxy, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

More preferably, $R^2$ is phenyl, thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, pyridazinyl, oxadiazolyl and thiadiazolyl, and N-oxides and salts thereof, where these rings are unsubstituted or substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

In even more preferred compounds of the formula I, $R^2$ is phenyl or pyridyl or phenyl or pyridyl both substituted by halogen, nitro, cyano, $C_1$-$C_2$alkyl, $C_1$-$C_2$haloalkyl, $C_1$-$C_2$alkoxy or $C_1$-$C_2$haloalkoxy.

In an especially preferred group of compounds, $R^2$ is phenyl substituted at the para-position by halogen (in particular chlorine) and is optionally further substituted by halogen, nitro, $C_1$-$C_2$alkyl, $C_1$-$C_2$haloalkyl, $C_1$-$C_2$alkoxy or $C_1$-$C_2$haloalkoxy.

Preferably, $R^3$ is hydrogen (r is 0), halogen or $C_1$-$C_6$alkyl, especially hydrogen.

Preferably, $R^3$, if r is 1, is halogen or $C_1$-$C_3$alkyl.

Preferred are those compounds of the formula I, wherein $R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$ alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl; $C_5$-$C_7$cycloalkyl or $C_5$-$C_7$cycloalkyl substituted by $C_1$- or $C_2$alkyl or $C_1$- or $C_2$haloalkyl and in which a methylene group is optionally replaced by an oxygen or sulfur atom or a sulfinyl or sulfonyl group; $C_5$-$C_7$cycloalkyl$C_1$-$C_5$alkyl or $C_5$-$C_7$cycloalkyl$C_1$-$C_5$alkyl substituted by $C_1$-$C_2$alkyl or $C_1$- or $C_2$haloalkyl and in which a methylene group is optionally replaced by an oxygen or sulfur atom or a sulfinyl or sulfonyl group.

More preferably, $R^4$, $R^5$, $R^6$ and $R^7$, independently of each other, are hydrogen, $C_1$-$C_2$alkyl, $C_1$-$C_2$haloalkyl or $C_1$-$C_2$alkoxy$C_1$-$C_2$alkyl.

Preferred meanings of Y are O, C=O and S.

Y is O is especially preferred.

Preferably, L is chloro, bromo or nitro.

In a preferred group of compounds of the formula (I), $R^1$ is $C_1$-$C_4$alkyl, $R^2$ is phenyl or phenyl substituted by halogen or $C_1$-$C_2$alkyl, $R^3$ is hydrogen, $R^4$, $R^5$, $R^6$ and $R^7$, independently of each other, are $C_1$-$C_2$alkyl, Y is O and L is chloro or nitro.

A compound of formula (I), wherein L is halogen, may be prepared by halogenating a compound of formula (A) with a suitable halogenating agent (such as chlorine, N-chlorosuccinimide, sulfuryl chloride, bromine or N-bromosuccinimide) in a suitable solvent (such as dichloromethane or chloroform).

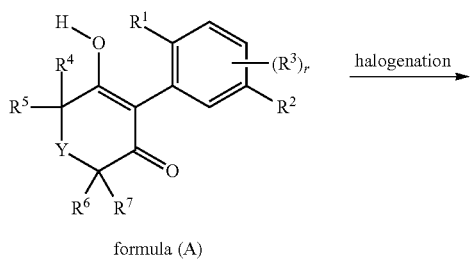

formula (A)

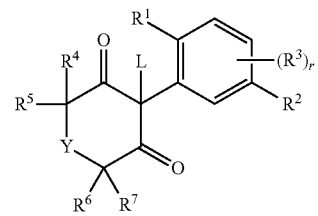

formula (I) wherein
L is a halogen

A compound of formula (I), wherein L is nitro, may be prepared by nitrating a compound of formula (A) with a suitable nitrating agent (such as a mixture of sodium nitrite and fuming nitric acid) in a suitable solvent (such as glacial acetic acid).

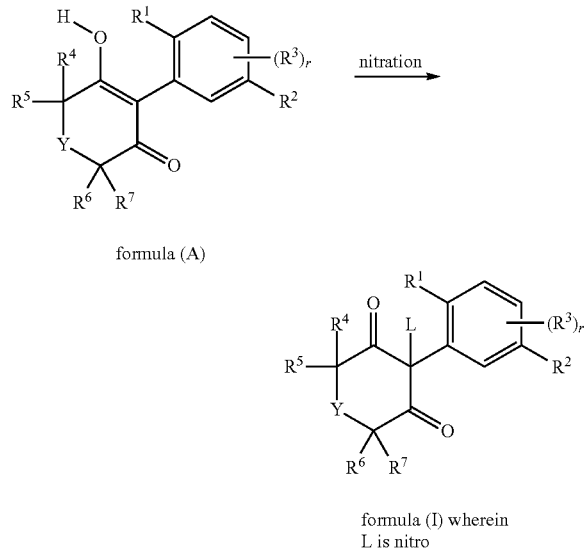

formula (A)

nitration formula (I) wherein
L is nitro

A compound of formula (I), wherein L is SO$_3$H, may be prepared by sulfonating a compound of formula (A) with a suitable sulfonating agent (such as concentrated sulphuric acid in the presence of acetic anhydride, chlorosulfonic acid, or dioxane-SO$_3$ complex), in a suitable solvent (such as dichloroethane or dioxane). Similar reactions are known in the literature (see for example, A. Strakov et al., Russian Journal of General Chemistry, (1960), 30, 3967).

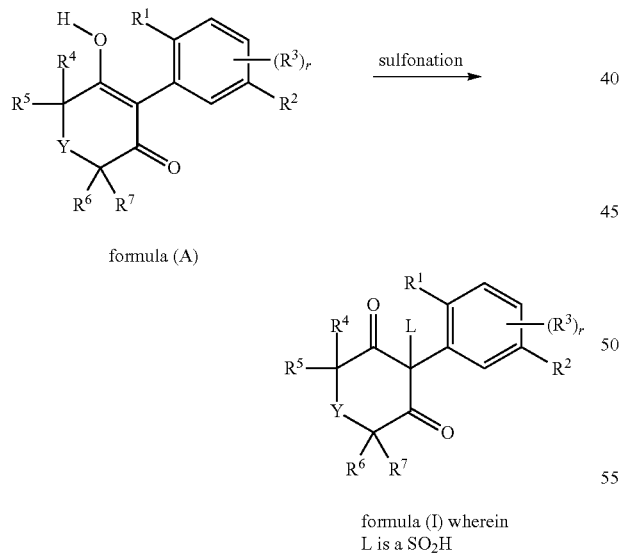

formula (A)

sulfonation formula (I) wherein
L is a SO$_2$H

A compound of formula (I), wherein L is $C_1$-$C_6$alkylthio, may be prepared by reacting a compound of formula (I), wherein L is halogen (preferably bromine), with a $C_1$-$C_6$-thiolate anion (generated for example by $C_1$-$C_6$alkylthiol in the presence of 1,8-diazabicyclo[5.4.0]undec-7-ene) in a suitable solvent (such as tetrahydrofuran). Similar reactions are known in the literature (see for example, K. Mitka et al., Acta Poloniae Pharmaceutica (2002), 59(5), 387).

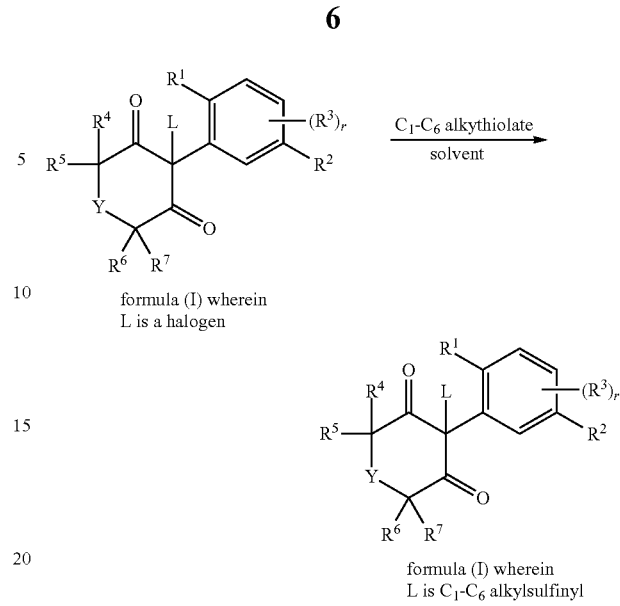

formula (I) wherein
L is a halogen $C_1$-$C_6$ alkythiolate
solvent formula (I) wherein
L is $C_1$-$C_6$ alkylsulfinyl A compound of formula (I), wherein L is SCN, may be prepared by reacting a compound of formula (A) with a thiocyanate salt (such as potassium thiocyanate or lead thiocyanate) in the presence of an oxidising agent (such as iodobenzene dichloride) in a suitable solvent (such as dichloroethane). Similar reactions are known in the literature (see for example, O. Prakash, et al., Synth. Commun. (2003), 33(23), 4037).

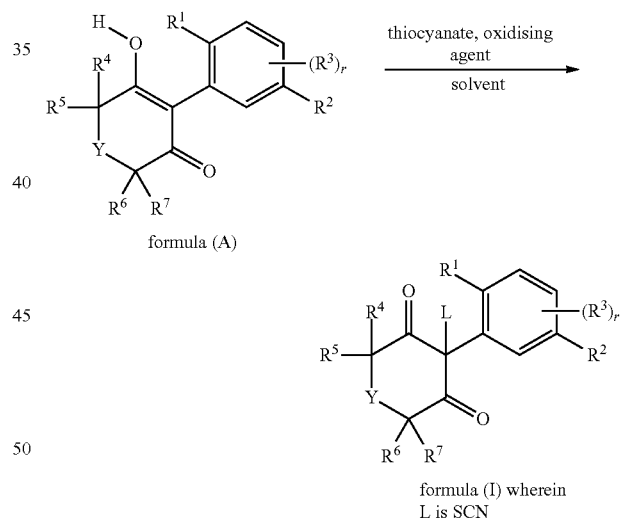

formula (A)

thiocyanate, oxidising
agent
solvent formula (I) wherein
L is SCN

Compounds of formula (A), wherein Y is S(O)$_m$ and m is 1 or 2 may be prepared from compounds of formula (A) wherein Y is S by oxidation, according to a procedure analogous to that of E. Fehnel and A. Paul, J. Am. Chem. Soc., (1955), 77, 4241.

A compound of formula (A), wherein Y is O, S or C=O may be prepared via the cyclisation of a compound of formula (B), preferably in the presence of an acid or base, and optionally in the presence of a suitable solvent, by analogous methods to those described by T. Wheeler, U.S. Pat. No. 4,209,532. Compounds of formula (B) wherein R is hydrogen or $C_1$-$C_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

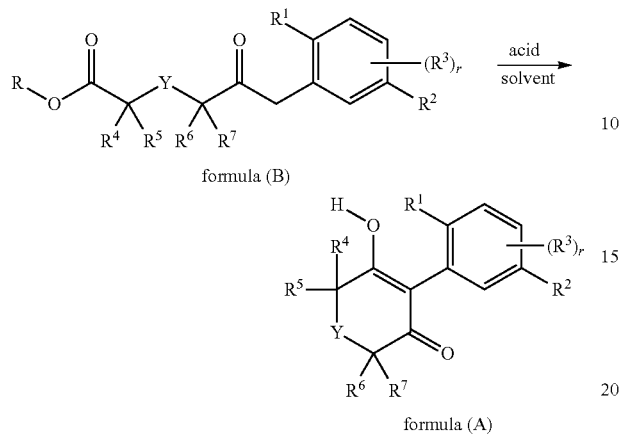

A compound of formula (B) wherein R is alkyl (preferably methyl or ethyl) may be cyclised under acidic or basic conditions, preferably under basic conditions in the presence of at least one equivalent of a strong base such as potassium tert-butoxide, lithium diisopropylamide, sodium bis(trimethylsilyl)amide or sodium hydride and in a solvent such as tetrahydrofuran, toluene, dimethylsulfoxide or N,N-dimethylformamide.

A compound of formula (B), wherein R is H may be esterified to a compound of formula (B), wherein R is alkyl, under known conditions (for example by treatment with an alcohol, R—OH, in the presence of an acid catalyst).

A compound of formula (B), wherein R is H may be prepared by hydrolysis of a compound of formula (C) wherein R is H or alkyl and R' is alkyl (preferably methyl or ethyl), followed by acidification of the reaction mixture to effect decarboxylation, by similar processes to those described by, for example, T. Wheeler, U.S. Pat. No. 4,209,532. Alternatively, a compound of formula (B), wherein R is alkyl (preferably methyl) may be prepared from a compound of formula (C), wherein R is alkyl (preferably methyl), through a Krapcho decarboxylation procedure under known conditions using known reagents (see for example G. Quallich, P. Morrissey, Synthesis, (1993), (1), 51).

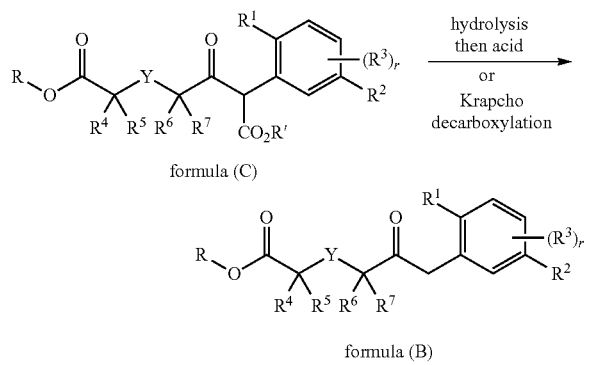

A compound of formula (C) wherein R is alkyl may be prepared by treating a compound of formula (D) with a suitable carboxylic acid chloride of formula (E) wherein R is alkyl under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C.:

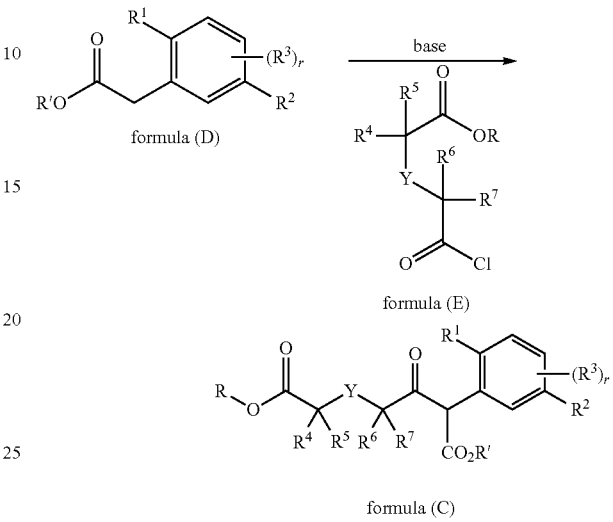

Alternatively, a compound of formula (C), wherein R is H, may be prepared by treating a compound of formula (D) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (F):

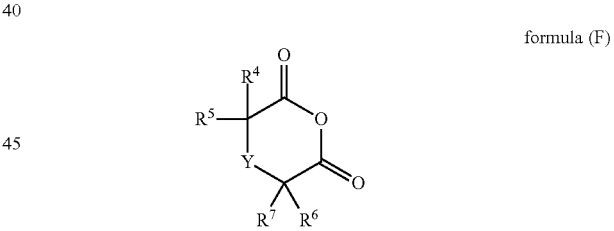

Compounds of formula (E) and formula (F) are known (see, for example T. Terasawa and T. Okada, J. Org. Chem., (1977), 42 (7), 1163 and G. Bennett, W. Houlihan, R. Mason, and R. Engstrom, J. Med. Chem., (1976), 19 (5), 709) or may be made by similar methods from commercially available starting materials.

Using similar procedures to those outlined above, and starting from a halogenated phenylacetic acid ester of formula (G) (wherein Hal is chlorine, bromine or iodine), a compound of formula (H) may be prepared. In turn, this may be converted into a compound of formula (A) where $R^2$ is an aryl or heteroaryl, by reaction with a coupling partner such as an aryl or heteroaryl boronic acid, $R^2$—$B(OH)_2$, or a suitable salt or ester thereof, under palladium-catalysed conditions, preferably Suzuki-Miyaura conditions.

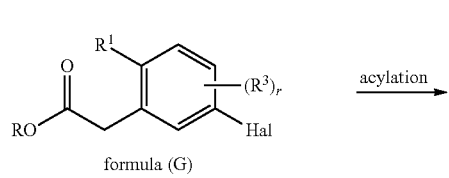

formula (G)

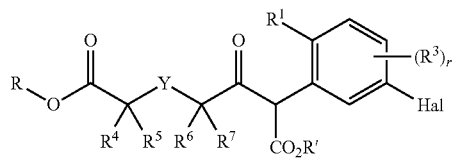

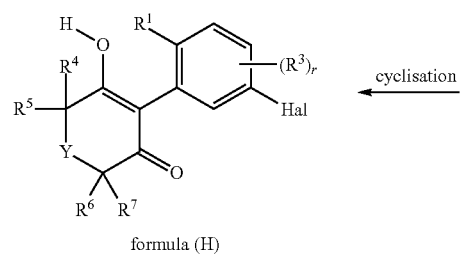

formula (H)

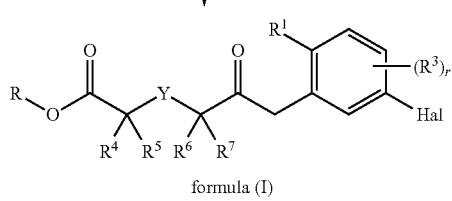

formula (I)

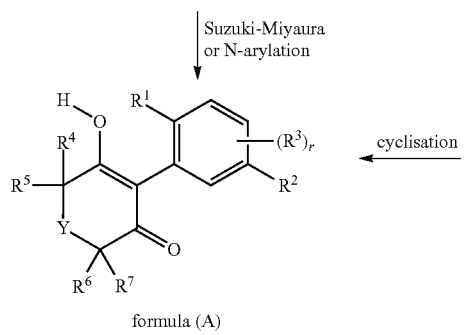

formula (A)

Conditions suitable for effecting the Suzuki-Miyaura cross-coupling of an aryl halide of formula (H) with an aryl- or heteroarylboronic acid of formula $R^2$—$B(OH)_2$, or a suitable salt or ester thereof, are known in the literature (see, for example K. Billingsley and S. Buchwald, J. Am. Chem. Soc., (2007), 129, 3358; H. Stefani, R. Cella and A. Vieira, Tetrahedron, (2007), 63, 3623; N. Kudo, M. Perseghini and G. Fu, Angew. Chem. Int. Ed., (2006), 45, 1282; A. Roglans, A. Pla-Quintana and M. Moreno-Mañas, Chem. Rev., (2006), 106, 4622; J-H Li, Q-M Zhu and Y-X Xie, Tetrahedron (2006), 10888; S, Nolan et al., J. Org. Chem., (2006), 71, 685; M. Lysén and K. Köhler, Synthesis, (2006), 4, 692; K. Anderson and S. Buchwald, Angew. Chem. Int. Ed., (2005), 44, 6173; Y. Wang and D. Sauer, Org. Lett., (2004), 6 (16), 2793; I. Kondolff, H. Doucet and M, Santelli, Tetrahedron, (2004), 60, 3813; F. Bellina, A. Carpita and R. Rossi, Synthesis (2004), 15, 2419; H. Stefani, G. Molander, C-S Yun, M. Ribagorda and B. Biolatto, J. Org. Chem., (2003), 68, 5534; A. Suzuki, Journal of Organometallic Chemistry, (2002), 653, 83; G. Molander and C-S Yun, Tetrahedron, (2002), 58, 1465; G. Zou, Y. K. Reddy and J. Falck, Tetrahedron Lett., (2001), 42, 4213; S. Darses, G. Michaud and J-P. Genêt, Eur. J. Org. Chem., (1999), 1877; M. Beavers et al., WO2005/012243; J. Org. Chem. (1994), 59, 6095; A. Collier and G. Wagner, Synthetic Communications, (2006), 36; 3713).

Alternatively, a compound of formula (A) may be prepared by a Suzuki-Miyaura cross-coupling of a compound of formula (I), wherein Hal is chlorine, bromine, iodine or a pseudohalogen such as $C_1$-$C_4$haloalkylsulfonate, especially triflate, with an aryl or heteroaryl boronic acid, of formula $R^2$—$B(OH)_2$, or a suitable salt or ester thereof, followed by cyclisation under conditions previously described for a compound of formula (B).

In a further approach, a compound of formula (A) wherein $R^2$ is an azine N-oxide such as a pyridine N-oxide, a pyrimidine N-oxide, pyridazine N-oxide or pyrazine N-oxide, may be prepared from a compound of formula (H) by reaction with a suitable azine-N-oxide under conditions described by L. Campeau, S. Rousseaux and K. Fagnou, J. Am. Chem. Soc., (2005), 127, 18020 and by J-P. Leclerc and K. Fagnou, Angew. Chem. Int. Ed., (2006), 45, 7781. The resulting N-oxide may be treated with known reagents under known conditions (for example reduction with hydrogen or ammonium formate in the presence of a suitable catalyst) to afford additional compounds of formula (I).

Additional compounds of formula (A), wherein $R^2$ is a heteroaromatic ring linked to the phenyl ring through a nitrogen atom, may be obtained by an Ullmann-type coupling (this reaction is also known in the literature as an N-arylation) of a compound of formula (H), or a compound of formula (I), with an N—H containing heteroaromatic compound, $R^2$—H, in the presence of a suitable catalyst, a suitable ligand, a suitable base and in a suitable solvent as described by, for example, M. Taillefer, N. Xia and A. Ouali, Angew. Chem. Int. Ed., (2007), 46 (6), 934; H. Zhang, Q. Cai, D. Ma, J. Org. Chem., (2005), 70, 5164; J. Antilla, J. Baskin, T. Barder and S. Buchwald, J. Org. Chem., (2004), 69, 5578 and A. Thomas and S. Ley, Angew. Chem. Int. Ed., 2003, 42, 5400 and references therein.

In a further approach, a compound of formula (A) wherein Y is O, S or C═O, may be prepared by reaction of a compound of formula (J) with an aryllead tricarboxylate, in the presence of a suitable ligand and in a suitable solvent. Similar reactions are described in the literature (for example see, J.

Pinhey, B. Rowe, Aust. J. Chem., (1979), 32, 1561; J. Morgan, J. Pinhey, J. Chem. Soc. Perkin Trans. 1, (1990), 3, 715). Preferably the aryllead tricarboxylate is an aryllead triacetate of formula (K). Preferably the ligand is a nitrogen containing heterocycle such as N,N-dimethylaminopyridine, 1,10-phenanthroline pyridine, bipyridine, or imidazole, and one to ten equivalents of ligand with respect to a compound of formula (J) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.).

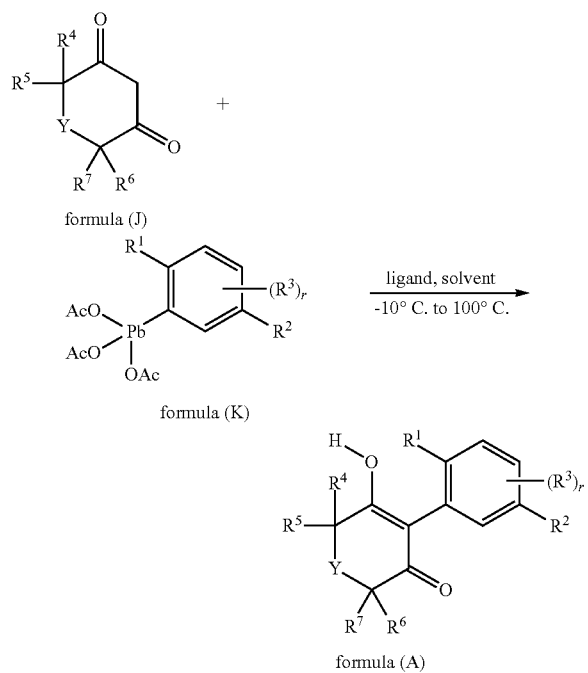

Compounds of formula (J), wherein Y is O, are known compounds or may be prepared by routes analogous to those described in the literature (see, for example, M. Morgan and E. Heyningen, J. Am. Chem Soc., (1957), 79, 422; I. Korobitsyna and K. Pivnitskii, Russian Journal of General Chemistry, (1960), 30, 4016; T. Terasawa, and T. Okada, J. Org. Chem., (1977), 42 (7), 1163; R. Anderson et al. U.S. Pat. No. 5,089,046; R. Altenbach, K. Agrios, I. Drizin and W. Carroll, Synth. Commun., (2004), 34 (4) 557; R. Beaudegnies et al., WO2005/123667; W. Li, G. Wayne, J. Lallaman, S. Chang, and S. Wittenberger, J. Org. Chem. (2006), 71, 1725; R. Altenbach, M. Brune, S. Buckner, M. Coghlan, A. Daza, A. Fabiyi, M. Gopalakrishnan, R. Henry, A. Khilevich, M. Kort, I. Milicic, V. Scott, J. Smith, K. Whiteaker, and W. Carroll, J. Med. Chem, (2006), 49(23), 6869; Carroll et al., WO 2001/083484 A1; J. Crandall, W. Conover, J. Org. Chem. (1978), 43(18), 3533; I. Korobitsyna, O, Studzinskii, Chemistry of Heterocyclic Compounds (1966), (6), 848). Compounds of formula (J), wherein Y is S, are known compounds or may be prepared by routes analogous to those described in the literature (see, for example, E. Fehnel and A. Paul, J. Am. Chem Soc., (1955), 77, 4241; E. Er and P. Margaretha, Helvetica Chimica Acta (1992), 75(7), 2265; H. Gayer et al., DE 3318648 A1). Compounds of formula (J), wherein Y is C=O, are known compounds or may be prepared by routes analo-gous to those described in the literature (see, for example, R. Götz and N. Götz, WO2001/060776 R. Götz et al. WO 2000/075095; M. Benbakkar et al., Synth. Commun. (1989) 19(18) 3241; A. Jain and T. Seshadri, Proc. Indian Acad. Sci. Sect. A, (1955), 42, 279); N. Ahmad et al., J. Org. Chem., (2007), 72(13), 4803; F. Effenberger et al., Chem. Ber., (1986), 119, 3394 and references therein).

A compound of formula (K) may be prepared from a compound of formula (L) by treatment with lead tetraacetate in a suitable solvent (for example chloroform) at 25° C. to 100° C. (preferably 25-50° C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407; J. Morgan and J. Pinhey, J. Chem. Soc. Perkin Trans. 1; (1990), 3, 715).

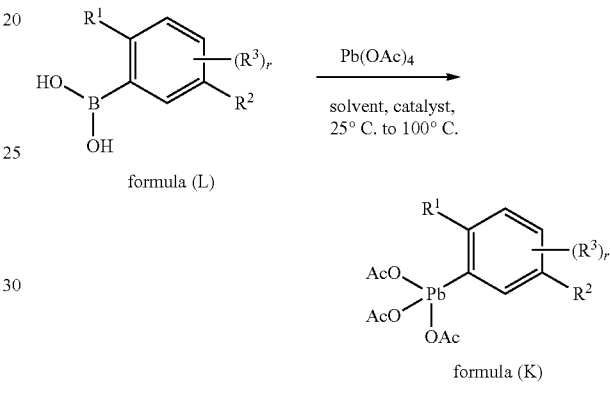

An aryl boronic acid of formula (L) may be prepared from an aryl halide of formula (M), wherein Hal is bromine or iodine by known methods (see, for example, W. Thompson and J. Gaudino, J. Org. Chem, (1984), 49, 5237 and R. Hawkins et al., J. Am. Chem. Soc., (1960), 82, 3053). Thus an aryl halide of formula (M) may be treated with an alkyl lithium or alkyl magnesium halide at low temperature, and the aryl magnesium or aryl lithium reagent obtained is allowed to react with a trialkyl borate, B(OR")$_3$, preferably trimethylborate, to give an aryl dialkylboronate which may be hydrolysed to the desired boronic acid of formula (L) under acidic conditions. Alternatively the same overall transformation of compound (M) to compound (L) may be achieved through a palladium-catalysed borylation reaction under known conditions using known reagents (see for example T. Ishiyama, M. Murata, N. Miyaura, J. Org. Chem. (1995), 60, 7508; and K. Billingsley, T. Barder, S. Buchwald, Angew. Chem. Int. Ed. (2007), 46, 5359), followed by hydrolysis of the intermediate boronate ester.

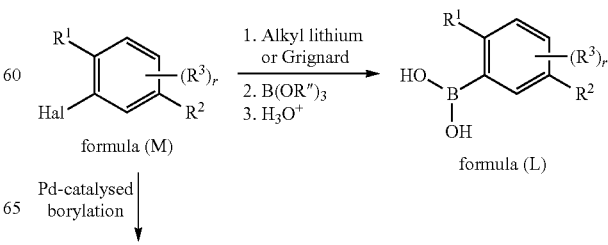

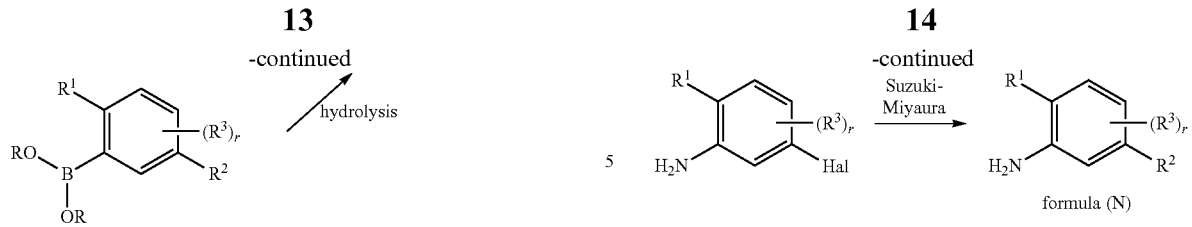

Aryl halides of formula (M) are known compounds or may be made by known methods from known compounds. For example, an aryl halide of formula (M) may be prepared from an aniline of formula (N) by known methods, for example the Sandmeyer reaction, via the corresponding diazonium salt (see, for example, J. March, Advanced Organic Chemistry, $3^{rd}$ Edition, John Wiley and Sons, p 647 and references therein. For additional examples see also W. Denney et al., J. Med. Chem., (1991), 34, 217; P. Knochel et al., Synthesis, (2007), No. 1, 81). Additionally, a compound of formula (N) may be converted directly to a compound of formula (L) via a palladium-catalysed borylation of an intermediate aryl diazonium salt under known conditions using known reagents (see for example D. Willis, R. Strongin, Tetrahedron Lett. (2000), 41, 8683), followed by hydrolysis of the intermediate boronate ester.

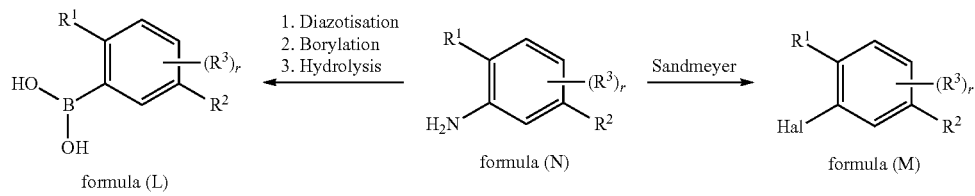

Anilines of formula (N) are known compounds, or may be made from known compounds by known methods. For example, an aniline of formula (N) may be prepared from an nitrobenzene of formula (O) (wherein Hal is chlorine, bromine, iodine, or a pseudohalogen such as $C_1$-$C_4$haloalkysulfonate, especially triflate) by reaction with an aryl- or heteroaryl-boronic acid, $R^2$—$B(OH)_2$, or a suitable salt or ester thereof, under Suzuki-Miyaura conditions, or with an N—H containing heteroaromatic ring, $R^2$—H, under N-arylation conditions, followed by reduction of the nitro group by standard methods. Alternatively, a compound of formula (O) may first be reduced to an aniline, and the aniline cross-coupled under Suzuki-Miyaura conditions (see, for example A. Maj, L. Delaude, A. Demonceau and A. Noels, Tetrahedron, (2007), 63, 2657; F. Bellina, A. Carpita and R. Rossi, Synthesis (2004), 15, 2419 and A. Suzuki, Journal of Organometallic Chemistry, (2002), 653, 83)

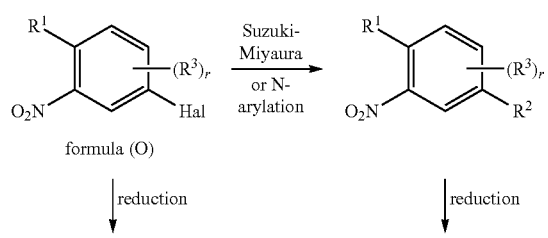

Nitrobenzenes of formula (O) are known compounds, or may be prepared from known compounds, by known methods.

In a further approach, a compound of formula (A) may be prepared from a compound of formula (P) by reaction with an aryl boronic acid of formula (L) in the presence of a suitable palladium catalyst and a base, preferably in a suitable solvent. Suitable palladium catalysts are generally palladium(II) or palladium(0) complexes, for example palladium(II) dihalides, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis(dibenzylideneacetone)palladium(0) or tetrakis(triphenylphosphine)palladium(0). The palladium catalyst can also be prepared "in situ" from palladium(II) or palladium(0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenylphosphine ($PPh_3$), tricyclopentylphosphine or tricyclohexylphosphine and the selected solvent, with a compound of formula (P), a compound of formula (L) and a base. Also suitable are bidendate ligands, for example 1, 1'-bis(diphenyl-phosphino)ferrocene or 1,2-bis(diphenylphosphino)ethane. By heating the reaction medium, the palladium(II) complex or palladium(0) complex desired for the C—C coupling reaction is thus formed "in situ", and then initiates the C—C coupling reaction.

The palladium catalysts are used in an amount of from 0.001 to 50 mol %, preferably in an amount of from 0.1 to 15 mol %, based on the compound of formula (P). More preferably the palladium source is palladium acetate, the base is lithium hydroxide and the solvent is a mixture of 1,2-dimethoxyethane and water in a ratio of 4:1 to 1:4. The reaction may also be carried out in the presence of other additives, such as tetralkylammonium salts, for example, tetrabutylammonium bromide:

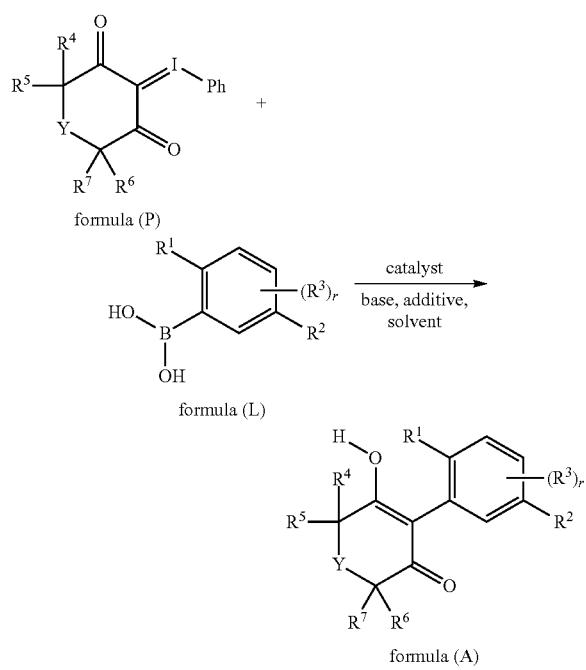

formula (P)

formula (L)

formula (A)

A compound of formula (P) may be prepared from a compound of formula (J) by treatment with (diacetoxy)iodobenzene according to the procedures of K. Schank and C. Lick, Synthesis, (1983), 392, or of Z Yang et al., Org. Lett., (2002), 4 (19), 3333:

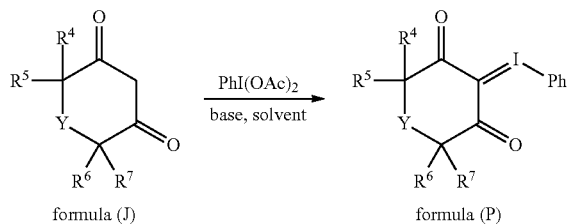

formula (J)   formula (P)

In a further approach a compound of formula (A) may be prepared via the rearrangement of a compound of formula (Q), in the presence of a reagent which promotes rearrangement, such as a metal alkoxide (preferably in an amount equal to or greater than 100% with respect to compound of formula (Q)) or cyanide anion (for example 0.001-25% potassium cyanide, 0.001-25% sodium cyanide), or a cyanohydrin (preferably 0.001-25% acetone cyanohydrin with respect to a compound of formula (Q)). This reaction is optionally performed in a suitable solvent (for example acetonitrile) at a suitable temperature (typically 25-100° C.) and with a suitable base (such as triethylamine).

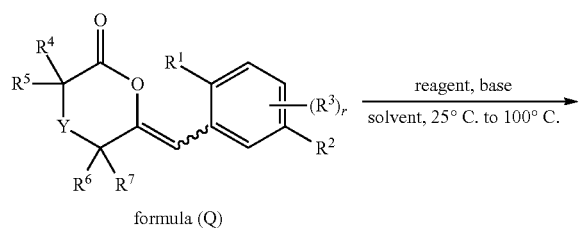

formula (Q)

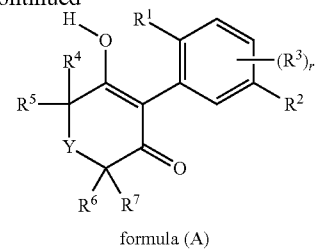

formula (A)

A compound of formula (Q) may be prepared from a compound of formula (R) by treatment with a catalyst which promotes lactonisation (such as palladium(II) dichloride, gold(I) chloride or silver carbonate), preferably 0.001-50% silver carbonate with respect to compound of formula (R), in the presence of a suitable solvent (for example acetonitrile) at a suitable temperature (typically 25° C. to 150° C.), and optionally under microwave irradiation. Similar lactonisations are known in the literature (see for example P. Huang and W. Zhou, Tetrahedron Asymmetry (1991), 2 (9), 875; and H. Harkat, J-M. Weibel, P. Pale, Tetrahedron Letters (2006), 47(35), 6273).

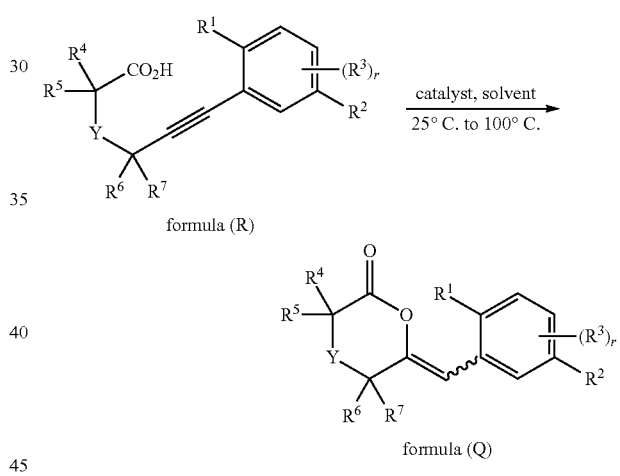

formula (R)

formula (Q)

A compound of formula (R) may be prepared by the hydrolysis of a compound of formula (S) where R' is alkyl (preferably methyl or ethyl), and a compound of formula (S) may be prepared from a compound of formula (T) by Sonogashira coupling with a compound of formula (M) in the presence of a suitable palladium catalyst (for example bis(triphenylphosphine)palladium(II) dichloride, tetrakis(triphenylphosphine)palladium(0) or palladium acetate in the presence of a suitable ligand), in an amount typically 0.001-25% of compound of formula (T), optionally in the presence of a suitable copper co-catalyst (for example copper(I) iodide in an amount typically 0.001-50% of compound of formula (T), a suitable base (such as diethylamine, triethylamine, piperidine or pyrrolidine) which may also be used as the solvent, or optionally in an alternative solvent such as 1,4-dioxane, N,N-dimethylacetamide or N,N-dimethylformamide, and optionally under microwave irradiation. Similar Sonogashira couplings are known in the literature (see for example see, J. Vara Prasad, F. Boyer, L. Chupak, M. Dermyer, Q. Ding, K. Gavardinas, S. Hagen, M. Huband, W. Jiao, T. Kaneko, S. Maiti, M. Melnick, K. Romero, M. Patterson, X. Wu, Bioorganic and Medicinal Chemistry Letters (2006), 16(20), 5392, N. Leadbeater and B. Tominack, Tetrahedron Lett., (2003), 8653, Z. Gan and R. Roy, Canadian Journal of Chemistry (2002), 80 (8), 908 and K. Sonogashira, J. Organomet. Chem., (2002), 653, 46 and references therein).

(U)) and preferably in the presence of a suitable ligand (for example 0.001-50% (2-dicyclohexylphosphino)-2',6'-dimethoxybiphenyl with respect to compound (U)), and in a suitable solvent (for example toluene), preferably between 25° C. and 200° C. Similar couplings are known in the literature (see for example, Y. Song, B. Kim and J.-N. Heo, Tetrahedron Letters (2005), 46 (36), 5987).

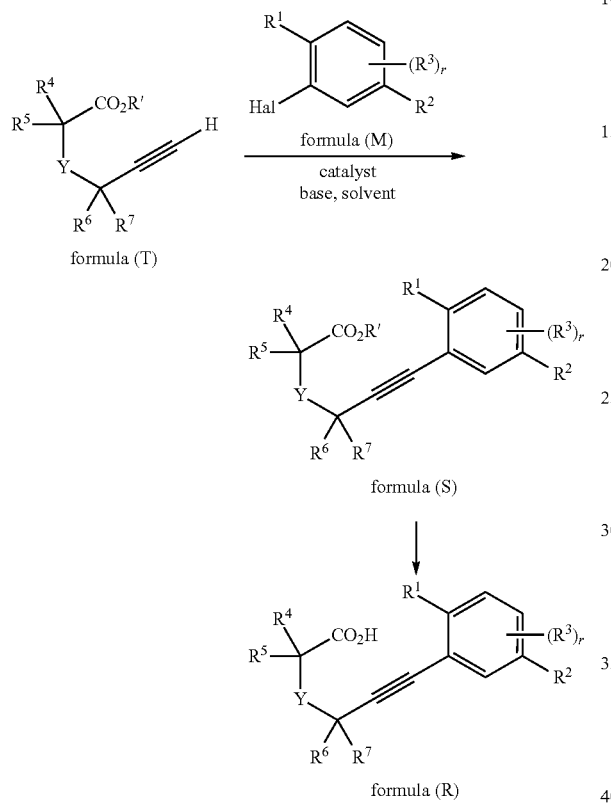

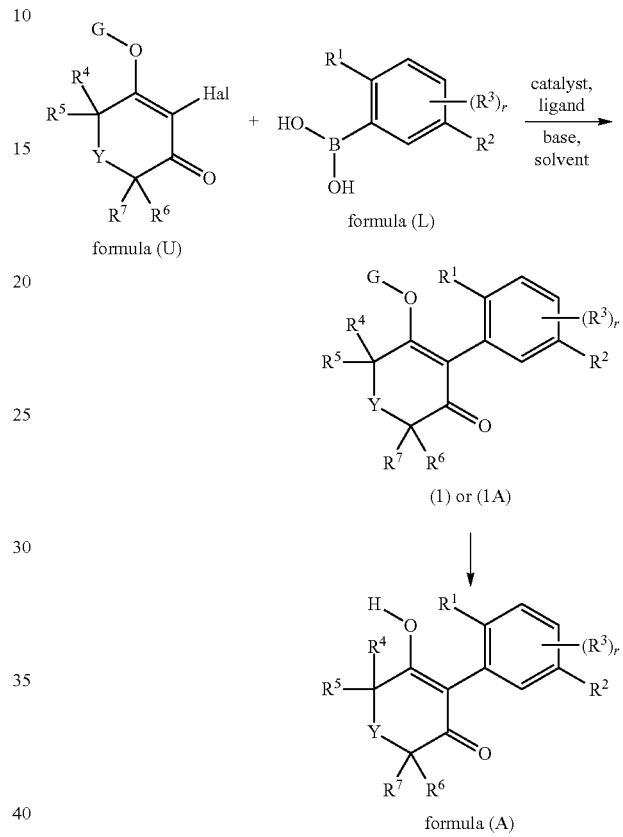

Compounds of formula (T) are known compounds or may be prepared by routes analogous to those described in the literature (see, for example, I. Drizin et al, WO2001/066544; M. Yamamoto, Journal of Chemical Research, Synopses (1991), (7), 165; P. Machin, U.S. Pat. No. 4,774,253; M. Morgan and E. Heyningen, J. Am. Chem Soc., (1957), 79, 422; N. Petiniot, A. Anciaux, A. Noels, A. Hubert, P. Teyssie, Tetrahedron letters, 1978, 14, 1239, and A. Noels, A. Demonceau, N. Petiniot, A. Hubert, P. Teyssie, Tetrahedron (1982), 38(17), 2733).

In a further approach, a compound of formula (A) may be prepared from a compound of formula (I) or (1A) (wherein G is $C_{1-4}$ alkyl) by hydrolysis, preferably in the presence of an acid catalyst such as hydrochloric acid and optionally in the presence of a suitable solvent such as tetrahydrofuran. A compound of formula (1) or (1A) (wherein G is preferably $C_{1-4}$ alkyl) may be prepared by reacting a compound of formula (U) (wherein G is preferably $C_{1-4}$ alkyl, and Hal is a halogen, preferably bromine or iodine), with an aryl boronic acid of formula (L) in the presence of a suitable palladium catalyst (for example 0.001-50% palladium(II) acetate with respect to compound (U)) and a base (for example 1 to 10 equivalents potassium phosphate with respect to compound A compound of formula (U) may be prepared by halogenating a compound of formula (J), followed by alkylation of the resulting halide of formula (V) with a $C_{1-4}$ alkyl halide or tri-$C_{1-4}$-alkylorthoformate under known conditions, for example by the procedures of R. Shepherd and A. White (J. Chem. Soc. Perkin Trans. 1 (1987), 2153) and Y.-L. Lin et al. (Bioorg. Med. Chem. (2002), 10, 685). Alternatively, a compound of formula (U) may be prepared by reacting a compound of formula (J) with an alkylating agent such as $C_{1-4}$ alkyl halide or a tri-$C_{1-4}$-alkylorthoformate, and halogenating the resulting enone of formula (W) under known conditions (see for example Y. Song, B. Kim and J.-N. Heo, Tetrahedron Letters (2005), 46(36), 5987).

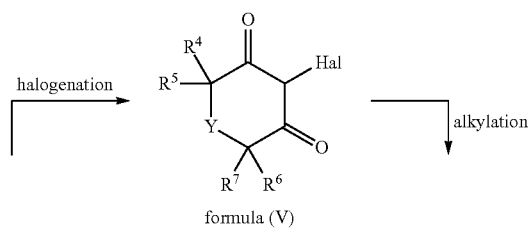

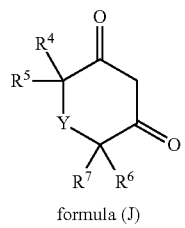
formula (J)

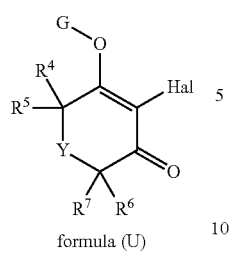
formula (U)

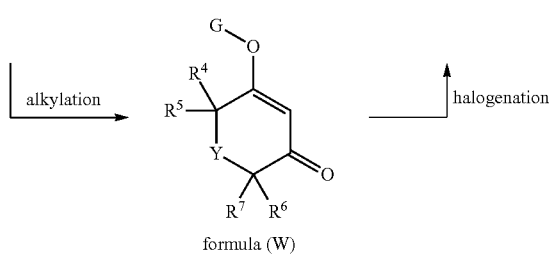
formula (W)

In a further approach, a compound of formula (A) may be prepared by reacting a compound of formula (J) with a compound of formula (M) in the presence of a suitable palladium catalyst (for example 0.001-50% palladium(II) acetate with respect to compound (J)) and a base (for example 1 to 10 equivalents potassium phosphate with respect to compound (J)) and preferably in the presence of a suitable ligand (for example 0.001-50% (2-dicyclohexylphosphino)-2',4',6'-triisopropylbiphenyl with respect to compound (J)), and in a suitable solvent (for example dioxane), preferably between 25° C. and 200° C. and optionally under microwave heating. Similar couplings are known in the literature (see for example, J. Fox, X. Huang, A. Chieffi, S. Buchwald, J. Am. Chem. Soc. (2000), 122, 1360; B. Hong et al. WO 2005/000233). Alternatively, a compound of formula (A) may be prepared by reacting a compound of formula (J) with a compound of formula (M) in the presence of a suitable copper catalyst (for example 0.001-50% copper(I) iodide with respect to compound (J)) and a base (for example 1 to 10 equivalents cesium carbonate with respect to compound (J)) and preferably in the presence of a suitable ligand (for example 0.001-50% L-proline with respect to compound (J)), and in a suitable solvent (for example dimethylsulfoxide), preferably between 25° C. and 200° C. Similar couplings are known in the literature (see for example, Y. Jiang, N. Wu, H. Wu, M. He, Synlett, (2005), 18, 2731, X. Xie, G. Cai, D. Ma, Organic Letters (2005), 7(21), 4693).

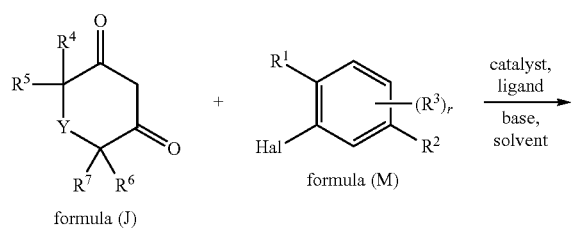
formula (J)    formula (M)

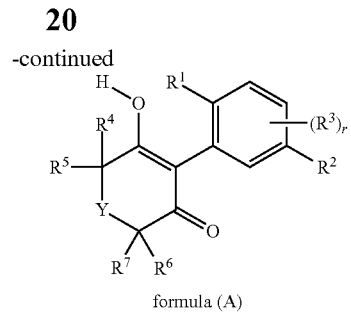
formula (A)

In a further approach, a compound of formula (A) may be prepared from a compound of formula (X) by cross coupling with an aryl- or heteroaryl-halide, R²-Hal, where Hal is preferably chlorine, bromine, iodine or a pseudohalide such as $C_1$-$C_4$haloalkylsulfonate, especially triflate, under Suzuki-Miyaura conditions described previously, or with an N—H containing heteroaromatic compound, R²—H, under copper-catalysed conditions as described, for example, by P. Lam et al., Tetrahedron Lett., (1998), 39 (19), 2941, and P. Lam, G. Vincent, C. G. Clark, S. Deudon, P. K. Jadhav, Tetrahedron Lett., (2001), 42, 3415.

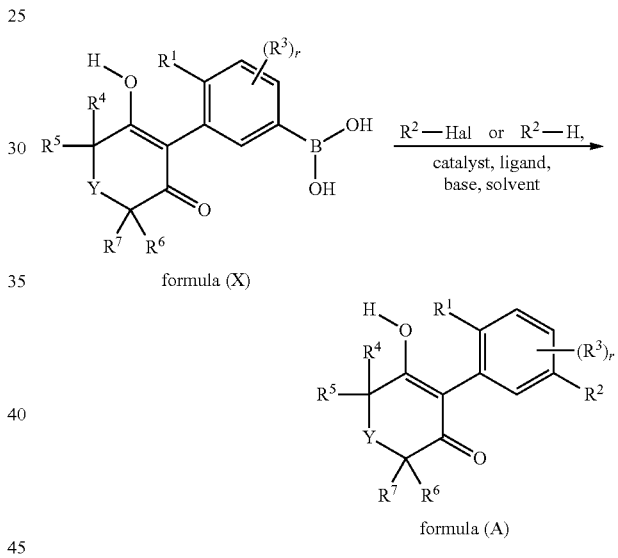
formula (X)

formula (A)

A compound of formula (X) may be prepared from a compound of formula (H) (wherein Hal is preferably iodine or bromine) by treatment with a suitable base (such as sodium hydride or potassium hydride), in a suitable solvent (such as tetrahydrofuran or diethyl ether) followed by a metal-halogen exchange reaction (preferably by treatment with an alkyl-lithium reagent such as n-butyllithium, sec-butyllithium or tert-butyllithium, or an organomagnesium reagent such as isopropyl magnesium chloride) and subsequent treatment with a trialkylborate, B(OR")₃, (preferably trimethylborate) to give an arylboronate of formula (Y). A compound of formula (Y) may be hydrolysed under acidic conditions to give a boronic acid of formula (X). Alternatively a compound of formula (X) may be prepared from a compound of formula (H) (wherein Hal is preferably iodine, bromine, chlorine or a pseudohalide such as a $C_1$-$C_4$haloalkylsulfonate, especially triflate) under known palladium-catalysed borylation conditions similar to those referenced for the preparation of compound (L).

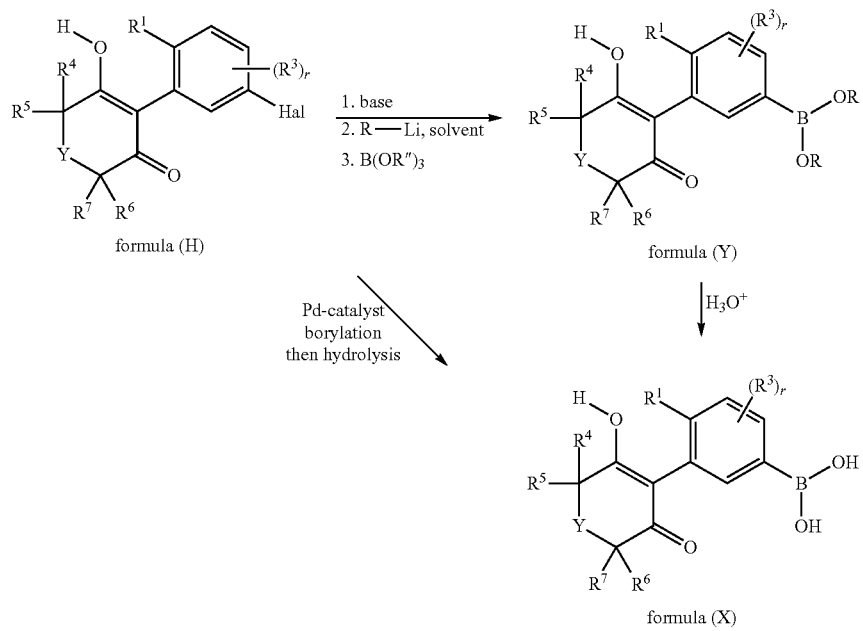
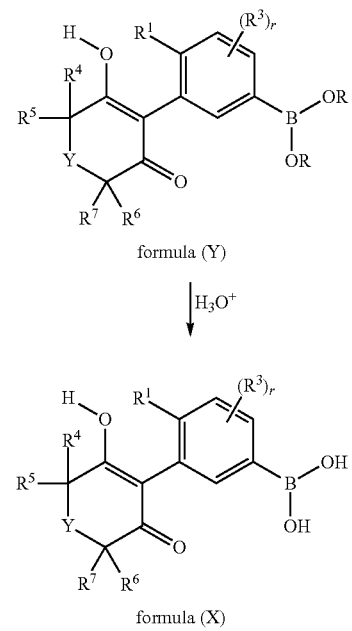

A compound of formula (H) may be prepared as described previously. Alternatively, a compound of formula (H) may be prepared from a compound of formula (J) by reaction with a compound of formula (Z) under conditions similar to those used for the preparation of a compound of formula (A) from a compound of formula (K).

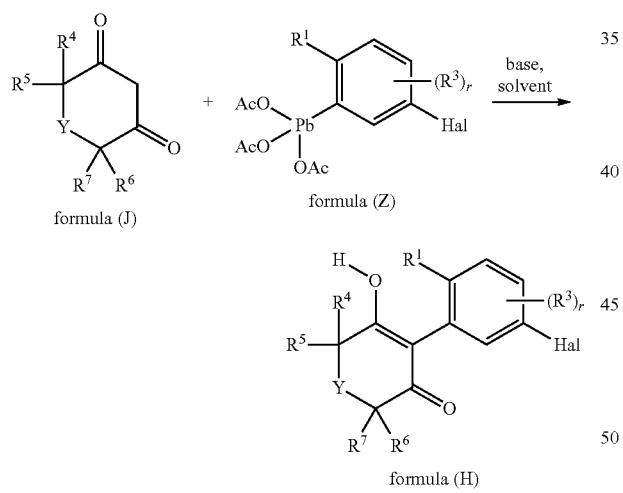

A compound of formula (Z) may be prepared from a compound of formula (Y) by methods similar to those described above for the preparation of a compound of formula (K) from a compound of formula (L).

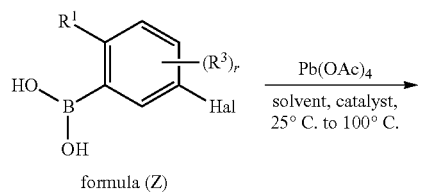

-continued

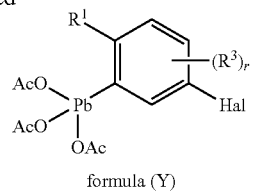

formula (Y)

Compounds of formula (Z) are known compounds (see, for example, R. Bhatt et al., US2004/0204386), or may be made by known methods from known compounds, as described, for example, for the preparation of compounds of formula (L).

The compounds of formula I according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution.

The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclo-hexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifiying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). Further oil additives that are preferred according to the invention are SCORE® (Syngenta Crop Protection Canada) and Adigor® (Syngenta Crop Protection Canada).

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1 to 4000 g/ha, especially from 5 to 1000 g/ha. Preferred formulations have especially the following compositions:

(%=percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. CaCO$_3$ or SiO$_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, which comprises treating the useful plants or the area under cultivation or the locus thereof with a compound of formula I.

Crops of useful plants in which the compositions according to the invention can be used include cereals, cotton, soybeans, sugar beet, sugar cane, plantation crops, rape, maize and rice, and for non-selective weed control. The compositions according to the invention are particularly useful for the selective control of grasses and weeds in cereals, maize and rice, especially rice. The term "crops" is to be understood as also including crops that have been rendered tolerant to herbicides or classes of herbicides (for example ALS, GS, EPSPS, PPO, ACCase and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with other herbicides. The following mixtures of the compound of formula I are especially important. Preferably, in these mixtures, the compound of the formula I is one of those compounds listed in Tables 1 to 210 below:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atrazine, formula I+aviglycine, formula I+azafenidin, compound of formula I+azimsulfuron, compound of formula I+BCPC, compound of formula I+beflubutamid, compound of formula I+benazolin, formula I+bencarbazone, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, formula I+bromophenoxim, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, formula I+desmetryn, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, formula I+dipropetryn, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, formula I+ethephon, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, formula I+fluazolate, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, formula I+flumetralin, compound of formula I+flumetsulam, compound of formula I+flumiclorac, compound of formula I+flumiclorac-pentyl, compound of formula I+flumioxazin, formula I+flumipropin, compound of formula I+fluometuron, compound of formula I+fluoroglycofen, compound of formula I+fluoroglycofen-ethyl, formula I+fluoxaprop, formula I+flupoxam, formula I+flupropacil, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, formula I+isoxapyrifop, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, formula I+methazole, compound of formula I+methylarsonic acid, compound of formula I+methyldymron, compound of formula I+methyl isothiocyanate, compound of formula I+metobenzuron, formula I+metobromuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, formula I+NDA-402989, compound of formula I+neburon, compound of formula I+nicosulfuron, formula I+nipyraclofen, formula I+n-methyl glyphosate, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, formula I+prohexadione-calcium, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, formula I+pyrasulfotole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, formula I+pyroxasulfone (KIN-485), formula I+pyroxulam, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, formula I+tebutam, compound of formula I+tebuthiuron, formula I+tefuryltrione, compound of formula I+tembotrione, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazafluoron, compound of formula I+thiazopyr, compound of formula I+thifensulfuron, compound of formula I+thiencarbazone, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+trinexapac-ethyl, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-hydroxy-3-[[2-[(2-methoxyethoxy)methyl]-6-(trifluoro-methyl)-3-pyridinyl]carbonyl]bicyclo[3.2.1]oct-3-en-2-one (CAS RN 352010-68-5), compound of formula 1+2-chloro-5-[3,6-dihydro-3-methyl-2,6-dioxo-4-(trifluoromethyl)-1(2H)-pyrimidinyl]-4-fluoro-N-[[methyl(1-methylethyl)amino]sulfonyl]-benzamide (CAS RN 372137-35-4), and compound of formula I+4-hydroxy-3-[[2-(3-methoxypropyl)-6-(difluoromethyl)-3-pyridinyl]carbonyl]bicyclo[3.2.1]oct-3-en-2-one.

The mixing partners for the compound of formula I may also be in the form of esters or salts, as mentioned e.g. in The Pesticide Manual, 12th Edition (BCPC) 2000.

The compounds of formula (I) according to the invention can also be used in combination with safeners. Preferably, in these mixtures, the compound of the formula (I) is one of those compounds listed in Tables 1 to 210 below. The following mixtures with safeners, especially, come into consideration:

compound of formula (I)+cloquintocet-mexyl, compound of formula (I)+cloquintocet acid and salts thereof, compound of formula (I)+fenchlorazole-ethyl, compound of formula (I)+fenchlorazole acid and salts thereof, compound of formula (I)+mefenpyr-diethyl, compound of formula (I)+mefenpyr diacid, compound of formula (I)+isoxadifen-ethyl, compound of formula (I)+isoxadifen acid, compound of formula (I)+furilazole, compound of formula (I)+furilazole R isomer, compound of formula (I)+benoxacor, compound of formula (I)+dichlormid, compound of formula (I)+AD-67, compound of formula (I)+oxabetrinil, compound of formula (I)+cyometrinil, compound of formula (I)+cyometrinil Z-isomer, compound of formula (I)+fenclorim, compound of formula (I)+cyprosulfamide, compound of formula (I)+naphthalic anhydride, compound of formula (I)+flurazole, compound of formula (I)+N-(2-methoxybenzoyl)-4-[(methylaminocarbonyl)amino]benzenesulfonamide, compound of formula (I)+CL 304,415, compound of formula (I)+dicyclonon, compound of formula (I)+fluxofenim, compound of formula (I)+DKA-24, compound of formula (I)+R-29148 and compound of formula (I)+PPG-1292. A safening effect can also be observed for the mixtures compound of the formula (I)+dymron, compound of the formula (I)+MCPA, compound of the formula (I)+mecoprop and compound of the formula (I)+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Preferred compositions according to the present invention contain in addition to comprising the compound of formula I, a further herbicide as mixing partner and a safener.

The following Examples illustrate the invention further but do not limit the invention.

PREPARATION EXAMPLES

Example 1

Preparation of 4-(2',4'-dichloro-4-ethylbiphen-3-yl)-2,2,6,6-tetramethyl-4-nitropyran-3,5-dione

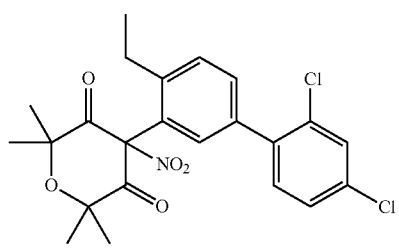

A1

Step 1: Preparation of 5-bromo-2-ethylaniline

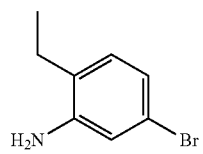

To a solution of 2-ethyl-5-bromo-1-nitrobenzene (9.71 g, 230 mmol) in ethanol (125 ml) is added tin(II) chloride dihydrate (35.72 g, 225.71 mmol), followed by heating at 70° C. for 2 hours. After cooling to room temperature the solution is poured into crushed ice (1 liter) then diluted with ethyl acetate (200 ml). Solid sodium carbonate is cautiously added until pH 7 is achieved, at which stage the viscous mixture is filtered through diatomaceous earth (further washing with ethyl acetate/aqueous sodium carbonate) and the phases separated. After additional extraction of the aqueous phase, all organic phases are combined, dried over anhydrous magnesium sulfate then concentrated in vacuo. The crude oil is purified by flash column chromatography on silica gel (hexane/ethyl acetate 8:2 ratio) to afford 5-bromo-2-ethylaniline (7.89 g) as a brown oil.

Step 2: Preparation of 4-bromo-1-ethyl-2-iodobenzene

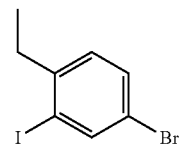

To a stirred mixture of 5-bromo-2-ethylaniline (3.39 g, 200 mmol) in distilled water (110 ml) is added concentrated sulfuric acid (5.60 ml), followed by brief heating at reflux until dissolution. The mixture is allowed to cool to room temperature, producing a fine precipitate, then further cooled to approximately 0° C. in an ice/salt bath. To this slurry is added an aqueous solution of sodium nitrite (1.17 g, 16.94 mmol) in distilled water (10 ml) dropwise over 15 minutes, maintaining a temperature below 5° C., followed by additional stirring for 30 minutes. The reaction mixture is next filtered then added to a second solution of aqueous potassium iodide (8.44 g, 50.83 mmol) in distilled water (45 ml) dropwise at room temperature. After the addition is complete the solution is briefly heated to 80° C. then allowed to cool to room temperature again. The reaction mixture is extracted with ethyl acetate (3×50 ml), and the organic phase is washed with 1M aqueous hydrochloric acid (30 ml) and aqueous sodium thiosulfate (2×30 ml). After drying over anhydrous magnesium sulfate and concentration in vacuo 4-bromo-1-ethyl-2-iodobenzene (4.90 g) is furnished as an orange liquid.

Step 3: Preparation of 5-bromo-2-ethylphenylboronic acid

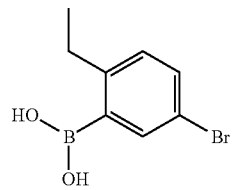

To a solution of 4-bromo-1-ethyl-2-iodobenzene (10.00 g, 32.20 mmol) in anhydrous tetrahydrofuran (60 ml) at −78° C. is added a solution of isopropylmagnesium chloride (16.90 ml, 33.80 mmol, 2M solution in tetrahydrofuran) dropwise, maintaining a temperature below −60° C.

After stirring for 20 minutes the reaction mixture is allowed to slowly warm to room temperature followed by an additional hour of stirring. The solution is re-cooled to −78° C. and trimethylborate (7.18 ml, 64.32 mmol) is added dropwise, after which the mixture is again allowed to warm to room temperature with further stirring for 2 hours. Dilute aqueous hydrochloric acid (30 ml) is added, and the crude product is extracted into ethyl acetate (100 ml). The aqueous phase is washed with ethyl acetate (2×100 ml), and all organics are combined, dried over anhydrous magnesium sulfate then concentrated in vacuo to give a light brown solid which is triturated with hexanes to afford 5-bromo-2-ethylphenylboronic acid (6.46 g) as a cream powder.

Step 4: Preparation of 5-bromo-2-ethylphenyllead triacetate

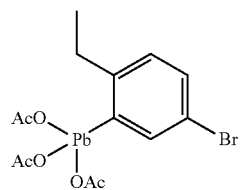

To a mixture of lead tetraacetate (13.7 g, 31.00 mmol) and mercuric diacetate (0.47 g, 1.50 mmol), thoroughly flushed with nitrogen, is added anhydrous chloroform (42 ml). This mixture is warmed to 40° C., and 5-bromo-2-ethylphenylboronic acid (6.50 g, 28.00 mmol) is added in one portion and the suspension is heated at this temperature for 5 hours. The mixture is then allowed to cool to room temperature, followed by further cooling to 0° C. then addition of powdered anhydrous potassium carbonate (3.22 g) with rapid stirring for 5 minutes then filtration. The filtrate is concentrated to half its volume, followed by the addition of hexanes to induce precipitation. This mixture is further concentrated, the solvent decanted, and the solid washed with hexanes to afford 5-bromo-2-ethylphenyllead triacetate (10.69 g) as a sandy coloured solid.

Step 5: Preparation of 4-(5-bromo-2-ethylphenyl)-2,2,6,6-tetramethylpyran-3,5-dione

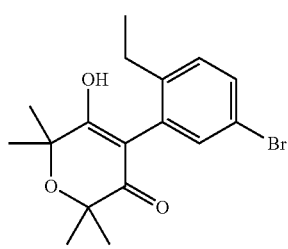 [SMILES: CCc1ccc(Br)cc1C1=C(O)C(C)(C)OC(C)(C)C1=O]

To a mixture of 2,2,6,6-tetramethylpyran-3,5-dione (3.57 g, 21.00 mmol) and N,N-dimethylaminopyridine (13.50 g, 111.00 mmol) is added anhydrous chloroform (120 ml), followed by stirring at room temperature until dissolution. To this solution is added anhydrous toluene (37 ml), followed by 5-bromo-2-ethylphenyllead triacetate (10.69 g, 24.00 mmol) in one portion and the reaction mixture is heated at 80° C. for 2 hours, then allowed to stand overnight at room temperature. The mixture is diluted with dichloromethane (185 ml) and dilute aqueous hydrochloric acid (185 ml), followed by swirling for 5 minutes and filtration to remove inorganic residues (additional washing with dichloromethane). All organic fractions are combined, washed with brine, dried over anhydrous magnesium sulfate, then concentrated in vacuo to afford a crude oil which is further purified by flash column chromatography (hexane/ethyl acetate 5:1 ratio) to give the product as a yellow solid (4.47 g). Lead residues are removed by dissolving this solid in chloroform (50 ml) and stirring with 3-mercaptopropyl-functionalized silica gel (5.50 g, 1.20 mmol/g loading) overnight. After filtration and concentration 4-(5-bromo-2-ethylphenyl)-2,2,6,6-tetramethylpyran-3,5-dione (4.36 g) is afforded as a cream powder.

Step 6: Preparation of 4-(2',4'-dichloro-4-ethylbiphen-3-yl)-2,2,6,6-tetramethylpyran-3,5-dione

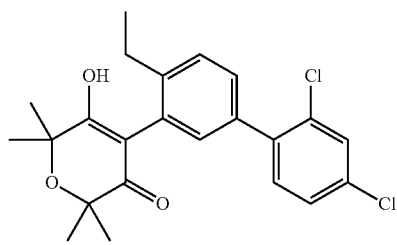 [SMILES: CCc1ccc(-c2ccc(Cl)cc2Cl)cc1C1=C(O)C(C)(C)OC(C)(C)C1=O]

To a mixture of 4-(5-bromo-2-ethylphenyl)-2,2,6,6-tetramethylpyran-3,5-dione (0.278 g, 0.79 mmol), cesium fluoride (1.19 g, 7.90 mmol) and 2,4-dichlorophenyl boronic acid (0.30 g, 1.58 mmol) is added degassed dioxane (2.5 ml), and the resulting suspension is stirred under nitrogen for 45 minutes over which time a milky suspension is formed. To this suspension is then added [1,1'-bis(diphenylphosphino)ferrocene]dichloropalladium(II) (0.102 g, 0.12 mmol) in one portion, and the mixture is heated at approximately 100° C. for 3 hours. After cooling to room temperature dichloromethane (150 ml) is added, and the solution washed with 1M hydrochloric acid (150 ml). The organic phase is separated, dried over anhydrous magnesium sulfate, filtered and the filtrate is concentrated in vacuo to afford a crude oil which is purified by column chromatography (hexane/ethyl acetate 5:1 ratio) to give the product as a foam. Trituration with hexanes affords 4-(2',4'-dichloro-4-ethylbiphen-3-yl)-2,2,6,6-tetramethylpyran-3,5-dione (0.250 g) as a white solid.

Step 7: Preparation of 4-(2',4'-dichloro-4-ethylbiphen-3-yl)-2,2,6,6-tetramethyl-4-nitropyran-3,5-dione

A1

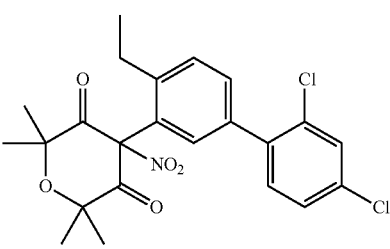

To a solution of 4-(2',4'-dichloro-4-ethylbiphen-3-yl)-2,2,6,6-tetramethylpyran-3,5-dione (0.200 g, 0.478 mmol) in glacial acetic acid (5 ml) is added sodium nitrite (0.0025 g, 0.036 mmol) then fuming nitric acid (0.12 ml). The mixture is stirred at room temperature for 2 hours, then the resulting slurry is poured into ice-water (50 ml). After swirling for 5 minutes the precipitate is filtered, dried, then washed with hexanes to afford 4-(2',4'-dichloro-4-ethyl-biphen-3-yl)-2,2, 6,6-tetramethyl-4-nitropyran-3,5-dione (0.201 g, 91%) as a yellow solid, m.p.=138-140° C.

1H NMR (CDCl$_3$) $\delta_H$ 7.50 (m, 3H), 7.32 (dd, 1H), 7.24 (d, 1H), 6.97 (s, 1H), 2.44 (q, 2H), 1.57 (s, 6H), 1.29 (s, 6H), 1.21 (t, 3H).

Example 2

Preparation of 4-chloro-4-(2',4'-dichloro-4-ethylbiphen-3-yl)-2,2,6,6-tetramethylpyran-3,5-dione

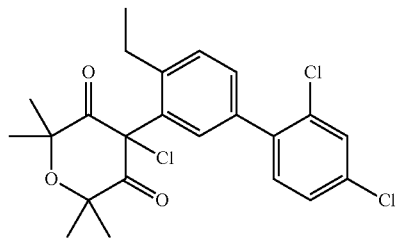

A2

To a solution of 4-(2',4'-dichloro-4-ethylbiphenyl-3-yl)-2,2,6,6-tetramethylpyran-3,5-dione (0.220 g, 0.525 mmol) in dry chloroform (4 ml) is added sulfuryl chloride (0.085 ml, 1.05 mmol), followed by stirring at room temperature for 4 hours. After dilution with diethyl ether (150 ml) the organic phase is washed with saturated sodium carbonate (150 ml) then dried over magnesium sulphate and the filtrate concentrated in vacuo to afford 4-chloro-4-(2',4'-dichloro-4-ethylbiphen-3-yl)-2,2,6,6-tetramethylpyran-3,5-dione (0.229 g, 96%) as a white solid.

1H NMR (CDCl$_3$) $\delta_H$ 7.49 (m, 1H), 7.44-7.43 (m, 2H), 7.36 (d, 1H), 7.29 (m, 2H), 2.38 (q, 2H), 1.62 (s, 6H), 1.46 (s, 6H), 1.20 (t, 3H).

Example 3

Preparation of 4-chloro-4-(4'-chloro-4-methylbiphenyl-3-yl)-2,2-dimethylpyran-3,5-dione

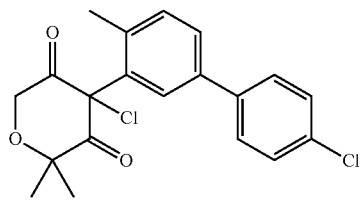

A3

Step 1: Preparation of [3-(4'-chloro-4-methylbiphenyl-3-yl)-1,1-dimethylprop-2-ynyloxy]acetic acid methyl ester

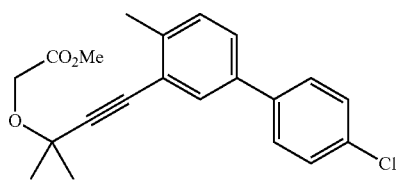 [SMILES: COC(=O)COC(C)(C)C#Cc1cc(-c2ccc(Cl)cc2)ccc1C]

To a solution of 3-bromo-4'-chloro-4-methylbiphenyl (12.6 g, 44.7 mmol) and (1,1-dimethylprop-2-ynyloxy)acetic acid methyl ester (prepared according to WO2001/066544) (8.4 g, 53.8 mmol) in triethylamine (70 ml) is added bis(triphenylphosphine)palladium(II) dichloride (0.63 g, 0.9 mmol) and copper(I) iodide (0.34 g, 1.8 mmol). The reaction mixture is degassed and flushed with nitrogen (×3), then stirred under nitrogen at 80° C. for one hour. The cooled mixture is filtered through diatomaceous earth to remove the catalyst, and the filtrate evaporated in vacuo. The residue is resubjected to the same reaction conditions (8.4 g 1,1-dimethylprop-2-ynyloxy)acetic acid methyl ester, 0.63 g bis(triphenylphosphine)-palladium(II) dichloride, 0.34 g copper (I) iodide in 70 ml triethylamine under nitrogen) and stirred at 80° C. for one hour. The cooled mixture is filtered through diatomaceous earth, then concentrated in vacuo and purified by flash chromatography (hexane/ethyl acetate 3:1) to afford [3-(4'-chloro-4-methylbiphenyl-3-yl)-1,1-dimethylprop-2-ynyloxy]acetic acid methyl ester (6.70 g,) as an oil.

Step 2: Preparation of [3-(4'-chloro-4-methylbiphenyl-3-yl)-1,1-dimethylprop-2-ynyloxy]acetic acid

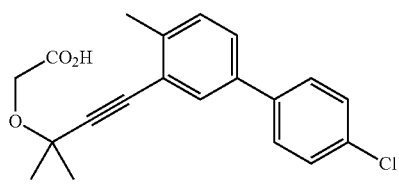 [SMILES: Cc1ccc(-c2ccc(Cl)cc2)cc1C#CC(C)(C)OCC(=O)O]

Potassium hydroxide (1.105 g, 19.7 mmol) is added to a solution of [3-(4'-chloro-4-methyl-biphenyl-3-yl)-1,1-dimethylprop-2-ynyloxy]acetic acid methyl ester (6.7 g, 18.8 mmol) in dioxane (20 ml) and water (20 ml). After stirring for four hours at 20° C., the reaction mixture is extracted twice with dichloromethane. The aqueous layer is acidified at 0° C. to pH 2-3 using 1N aqueous hydrochloric acid and extracted twice with ethyl acetate. The combined organic extracts are dried over anhydrous sodium sulfate, filtered and the filtrate evaporated in vacuo. The residue is stirred in hexane and filtered to afford [3-(4'-chloro-4-methylbiphenyl-3-yl)-1,1-dimethylprop-2-ynyloxy]acetic acid (4.50 g) as a white solid (m.p. 125° C.).

Step 3: Preparation of 6-[1-(4'-chloro-4-methylbiphenyl-3-yl)methylidene]-5,5-dimethyl-[1,4]dioxan-2-one

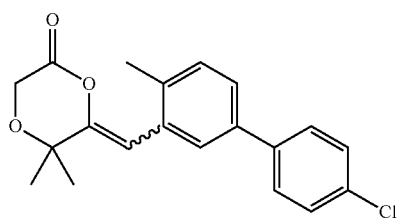 [SMILES: Cc1ccc(-c2ccc(Cl)cc2)cc1C=C1OC(=O)COC1(C)C]

Silver carbonate (0.17 g, 0.61 mmol) is added to a solution of [3-(4'-chloro-4-methyl-biphenyl-3-yl)-1,1-dimethylprop-2-ynyloxy]acetic acid (2.1 g, 6.13 mmol) in anhydrous acetonitrile (15 ml) in a microwave vial. The reaction mixture is stirred and heated to 120° C. for 40 minutes under microwave irradiation to give a brown suspension. The mixture is evaporated in vacuo, then diluted with water and extracted with ethyl acetate. The combined organic extracts are dried over anhydrous sodium sulfate, filtered and the filtrate evaporated in vacuo to give 6-[1-(4'-chloro-4-methylbiphenyl-3-yl)methylidene]-5,5-dimethyl-[1,4]dioxan-2-one (1.75 g) as a solid.

Step 4: Preparation of 4-(4'-chloro-4-methylbiphenyl-3-yl)-2,2-dimethylpyran-3,5-dione

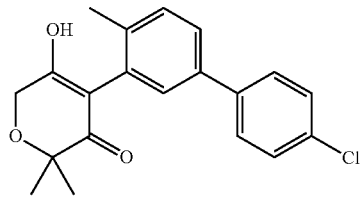 [SMILES: Cc1ccc(-c2ccc(Cl)cc2)cc1C1=C(O)COC(C)(C)C1=O]

To a suspension of 6-[1-(4'-chloro-4-methylbiphenyl-3-yl)methylidene]-5,5-dimethyl-[1,4]dioxan-2-one (1.5 g, 4.38 mmol) in anhydrous acetonitrile (22 ml) is added triethylamine (0.67 ml, 4.81 mmol) and potassium cyanide (30 mg, 0.46 mmol). The reaction mixture is stirred under reflux for two hours. The cooled mixture is diluted with ethyl acetate, and 0.5N aqueous hydrochloric acid is added at 0° C. The organic layer is separated and the aqueous phase extracted twice with ethyl acetate. The combined organic extracts are dried over anhydrous sodium sulfate, filtered and the filtrate evaporated in vacuo. The residue is purified by flash chromatography (heptane/ethyl acetate 1:1 ratio) to afford 4-(4'-chloro-4-methylbiphenyl-3-yl)-2,2-dimethylpyran-3,5-dione (1.35 g) as a foam. A sample of the product is stirred in hexane/diisopropyl ether (4:1 ratio) and filtered to give a white solid with a melting point of 186-188° C.

Step 5: Preparation of 4-chloro-4-(4'-chloro-4-methylbiphenyl-3-yl)-2,2-dimethylpyran-3,5-dione

A3

Final chlorination as described for compound A2.

δ 7.50 (dd, 1H), 7.49-7.44 (m, 3H), 7.43-7.37 (m, 2H), 7.28 (d, 1H), 4.58 (d, 1H), 4.54 (d, 1H), 2.20 (s, 3H), 1.53 (s, 3H), 1.46 (s, 3H).

Example 4

Preparation of 4-Chloro-4-(4'-chloro-4-methylbiphenyl-3-yl)-2,2,6,6-tetramethyl-pyran-3,5-dione

A4

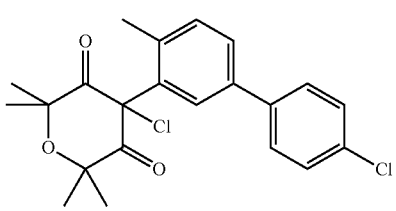

Step 1: Preparation of 3-amino-4'-chloro-4-methylbiphenyl

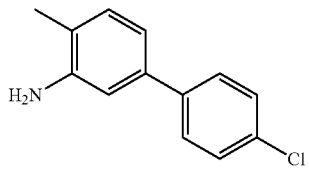

Tetrakis(triphenylphosphine)palladium (0) (3.7 g, 0.003 mol) and 4-chlorophenylboronic acid (20.2 g, 0.13 mol) are added to a solution of 5-bromo-2-methylaniline (20 g, 0.1 mol) in 1,2-dimethoxyethane (200 ml). After stirring the reaction mixture for 15 minutes at 20° C., a solution of 20% aqueous sodium carbonate (300 ml) is added to the mixture, and the resulting mixture is heated at reflux for 24 hours. The reaction mixture is cooled to room temperature, diluted with water (600 ml) and extracted using ethyl acetate. The combined organic extracts are dried over anhydrous sodium sulfate, filtered and the filtrate evaporated in vacuo. The residue is further purified by column chromatography on silica gel, eluting with 7% ethyl acetate in hexane to give 3-amino-4'-chloro-4-methylbiphenyl (21.0 g).

Step 2: Preparation of 3-bromo-4'-chloro-4-methylbiphenyl

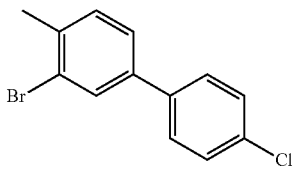

Hydrobromic acid (48% wt. in water, 120 ml) is added dropwise to a suspension of 3-amino-4'-chloro-4-methylbiphenyl (21 g, 0.09 mol) in water (80 ml), and the mixture stirred until the solid is dissolved. The mixture is cooled to −5° C. and a solution of sodium nitrite (10.12 g, 0.14 mol) in water (50 ml) is added dropwise, maintaining the temperature at 0-5° C. The reaction mixture is stirred for 1 hour, then added to a pre-cooled solution of cuprous bromide (17.9 g, 0.12 mol) in hydrobromic acid (48% wt. in water, 120 ml) at 0° C. The reaction mixture is stirred and allowed to warm to room temperature overnight. The mixture is extracted with ethyl acetate, and the organic extracts are combined, dried over anhydrous sodium sulfate, filtered and the filtrate concentrated in vacuo. The residue is further purified by column chromatography on silica gel, eluting with 2% ethyl acetate in hexane to give 3-bromo-4'-chloro-4-methylbiphenyl (15.0 g).

Step 3: Preparation of 4'-chloro-4-methylbiphenyl-3-ylboronic acid

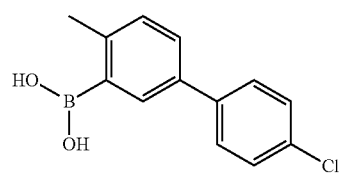 [SMILES: Cc1ccc(-c2ccc(Cl)cc2)cc1B(O)O]

3-Bromo-4'-chloro-4-methylbiphenyl (5.0 g, 0.02 mol) is dissolved in anhydrous tetrahydrofuran (125 ml), and the mixture is cooled to −78° C. n-Butyllithium (1.33 molar solution in hexanes, 17.3 ml,) is added dropwise over 30 minutes, maintaining the temperature at approximately −78° C. The reaction mixture is stirred for one and a half hours at −78° C., then trimethylborate (2.58 g, 0.024 mol) is added dropwise and the reaction mixture stirred for three and a half hours, allowing it to warm to 0° C. A solution of 2N aqueous hydrochloric acid (50 ml) is then added dropwise, and once the addition is complete the mixture is stirred for 2 hours. The mixture is concentrated in vacuo to remove most of the tetrahydrofuran, then diluted with water (~80 ml) and extracted with diethyl ether. The organic extracts are combined, dried over anhydrous sodium sulfate, filtered and the filtrate evaporated in vacuo. The residue is further purified by flash column chromatography on silica gel, eluting with 7% ethyl acetate in hexane to give 4'-chloro-4-methylbiphenyl-3-ylboronic acid (2.5 g).

Step 4: Preparation of 4'-chloro-4-methylbiphenyl-3-yllead triacetate

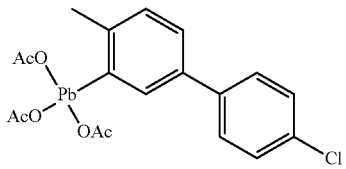

Step 4a

To a mixture of lead tetraacetate (2.44 g, 5.50 mmol) and mercuric diacetate (0.16 g, 0.50 mmol), thoroughly flushed with nitrogen, is added anhydrous chloroform (6 ml). This mixture is warmed to 40° C., and 4'-chloro-4-methylbiphenyl-3-ylboronic acid (1.23 g, 5.00 mmol) is added in one portion, and the suspension is heated at this temperature for 5 hours. After cooling to room temperature the mixture is concentrated to a small volume, then triturated with hexanes and filtered to yield crude 4'-chloro-4-methylbiphenyl-3-yllead triacetate (2.93 g).

Step 4b

Crude 4'-chloro-4-methyl-biphenyl-3-yllead triacetate (1.50 g) is dissolved in anhydrous chloroform (20 ml), to which is added powdered anhydrous potassium carbonate (0.59 g, 4.24 mmol) followed by rapid stirring for 5 minutes. Solids are removed by filtration, and the organic solution is concentrated to afford pure 4'-chloro-4-methylbiphenyl-3-yllead triacetate (1.121 g) as a bright orange solid.

Step 5: Preparation of 4-(4'-chloro-4-methylbiphenyl-3-yl)-2,2,6,6-tetramethylpyran-3,5-dione

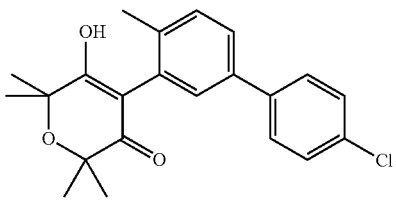 [SMILES: Cc1ccc(-c2ccc(Cl)cc2)cc1C1=C(O)C(C)(C)OC(C)(C)C1=O]

To a mixture of 2,2,6,6-tetramethylpyran-3,5-dione (described in U.S. Pat. No. 5,089,046A) (0.296 g, 1.74 mmol) and N,N-dimethylaminopyridine (1.06 g, 8.70 mmol) is added anhydrous chloroform (20 ml), followed by stirring at room temperature until dissolution. To this solution is added anhydrous toluene (5 ml), followed by 4'-chloro-4-methylbiphenyl-3-yllead triacetate (1.12 g, 1.91 mmol) in one portion and the reaction mixture heated at 80° C. for 1-2 hours. The mixture is allowed to cool to room temperature, then diluted with dichloromethane (150 ml) and dilute aqueous hydrochloric acid (30 ml), followed by stirring for 5 minutes and filtration through diatomaceous earth to remove inorganic residues (additional washing with solvents). All organic fractions are combined, dried over anhydrous magnesium sulfate and concentrated in vacuo. The crude product is purified by column chromatography (100% hexane to hexane/ethyl acetate 5:1 ratio) then triturated with hexanes to afford 4-(4'-chloro-4-methylbiphenyl-3-yl)-2,2,6,6-tetramethylpyran-3,5-dione (0.318 g) as a cream powder.

Step 6: Preparation of 4-Chloro-4-(4'-chloro-4-methylbiphenyl-3-yl)-2,2,6,6-tetramethyl-pyran-3,5-dione

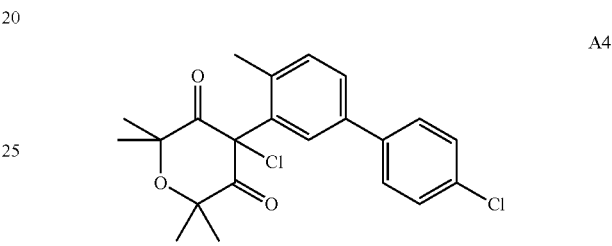

A4

To a solution of 4-(4'-chloro-4-methylbiphenyl-3-yl)-2,2,6,6-tetramethylpyran-3,5-dione in anhydrous chloroform (3 ml) at 0° C. is added a second solution of sulfuryl chloride (0.025 ml, 0.315 mmol) in anhydrous chloroform (0.3 ml) dropwise. The reaction mixture is stirred for 30 minutes at 0° C. then for a further 1 hour at room temperature. Additional sulfuryl chloride (0.025 ml, 0.315 mmol) is next added, followed by warming to 60° C. for 2 hours, followed by addition of further sulfuryl chloride (0.20 ml, 2.52 mmol). The reaction mixture is finally stirred at room temperature overnight then quenched with saturated aqueous sodium bicarbonate, and extracted with ethylacetate. Purification by flash column chromatography (20% ethylacetate in hexane eluant) afforded 4-chloro-4-(4'-chloro-4-methylbiphenyl-3-yl)-2,2,6,6-tetramethyl-pyran-3,5-dione (0.033 g) as a yellow oil.

1H NMR (CDCl$_3$) δ$_H$ 7.51 (d, 1H), 7.48 (m, 3H), 7.40 (m, 2H), 7.26 (d, 1H), 2.18 (s, 3H), 1.60 (s, 6H), 1.46 (s, 6H).

TABLE 1

This table covers 378 compounds of the type (T-1):

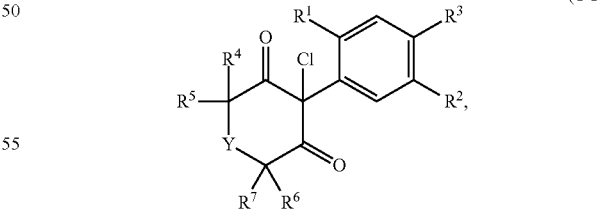

(T-1)

wherein Y is O, R$^1$ is methyl, R$^4$, R$^5$, R$^6$ and R$^7$ are hydrogen, and R$^2$ and R$^3$ are as defined below:

| Compound Number | R$^2$ | R$^3$ |
|---|---|---|
| 1.001 | phenyl | H |
| 1.002 | 2-fluorophenyl | H |
| 1.003 | 3-fluorophenyl | H |
| 1.004 | 4-fluorophenyl | H |
| 1.005 | 2-chlorophenyl | H |
| 1.006 | 3-chlorophenyl | H |

TABLE 1-continued

This table covers 378 compounds of the type (T-1):

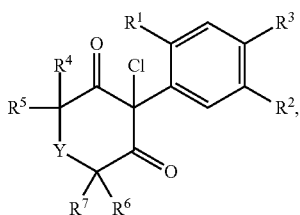

(T-1)

wherein Y is O, $R^1$ is methyl, $R^4$, $R^5$, $R^6$ and $R^7$ are hydrogen, and $R^2$ and $R^3$ are as defined below:

| Compound Number | $R^2$ | $R^3$ |
|---|---|---|
| 1.007 | 4-chlorophenyl | H |
| 1.008 | 2-bromophenyl | H |
| 1.009 | 3-bromophenyl | H |
| 1.010 | 4-bromophenyl | H |
| 1.011 | 4-tert-butyl | H |
| 1.012 | 2-iodophenyl | H |
| 1.013 | 3-iodophenyl | H |
| 1.014 | 4-iodophenyl | H |
| 1.015 | 2-methylphenyl | H |
| 1.016 | 3-methylphenyl | H |
| 1.017 | 4-methylphenyl | H |
| 1.018 | 2-cyanophenyl | H |
| 1.019 | 3-cyanophenyl | H |
| 1.020 | 4-cyanophenyl | H |
| 1.021 | 2-methoxyphenyl | H |
| 1.022 | 3-methoxyphenyl | H |
| 1.023 | 4-methoxyphenyl | H |
| 1.024 | 2-difluoromethoxyphenyl | H |
| 1.025 | 3-difluoromethoxyphenyl | H |
| 1.026 | 4-difluoromethoxyphenyl | H |
| 1.027 | 2-difluoromethylphenyl | H |
| 1.028 | 3-difluoromethylphenyl | H |
| 1.029 | 4-difluoromethylphenyl | H |
| 1.030 | 2-trifluoromethylphenyl | H |
| 1.031 | 3-trifluoromethylphenyl | H |
| 1.032 | 4-trifluoromethylphenyl | H |
| 1.033 | 2-trifluoromethoxyphenyl | H |
| 1.034 | 3-trifluoromethoxyphenyl | H |
| 1.035 | 4-trifluoromethoxyphenyl | H |
| 1.036 | 4-methylthiophenyl | H |
| 1.037 | 4-methylsulfinylphenyl | H |
| 1.038 | 4-methylsulfonylphenyl | H |
| 1.039 | 4-trifluoromethylthiophenyl | H |
| 1.040 | 4-trifluoromethylsulfinylphenyl | H |
| 1.041 | 4-trifluoromethylsulfonylphenyl | H |
| 1.042 | 2,3-difluorophenyl | H |
| 1.043 | 2,4-difluorophenyl | H |
| 1.044 | 2,5-difluorophenyl | H |
| 1.045 | 2,6-difluorophenyl | H |
| 1.046 | 3,4-difluorophenyl | H |
| 1.047 | 3,5-difluorophenyl | H |
| 1.048 | 2,3-dichlorophenyl | H |
| 1.049 | 2,4-dichlorophenyl | H |
| 1.050 | 2,5-dichlorophenyl | H |
| 1.051 | 2,6-dichlorophenyl | H |
| 1.052 | 3,4-dichlorophenyl | H |
| 1.053 | 3,5-dichlorophenyl | H |
| 1.054 | 4-chloro-2-cyanophenyl | H |
| 1.055 | 4-chloro-3-cyanophenyl | H |
| 1.056 | 4-chloro-2-fluorophenyl | H |
| 1.057 | 4-chloro-3-fluorophenyl | H |
| 1.058 | 4-chloro-2-methoxyphenyl | H |
| 1.059 | 4-chloro-3-methoxyphenyl | H |
| 1.060 | 4-chloro-2-methylphenyl | H |
| 1.061 | 4-chloro-3-methylphenyl | H |
| 1.062 | 4-chloro-2-difluoromethoxyphenyl | H |
| 1.063 | 4-chloro-3-difluoromethoxyphenyl | H |
| 1.064 | 4-chloro-2-trifluoromethoxyphenyl | H |
| 1.065 | 4-chloro-3-trifluoromethoxyphenyl | H |
| 1.066 | 4-chloro-2-difluoromethylphenyl | H |
| 1.067 | 4-chloro-3-difluoromethylphenyl | H |
| 1.068 | 4-chloro-2-trifluoromethylphenyl | H |
| 1.069 | 4-chloro-3-trifluoromethylphenyl | H |

TABLE 1-continued

This table covers 378 compounds of the type (T-1):

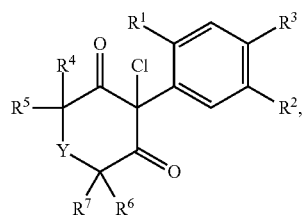

(T-1)

wherein Y is O, $R^1$ is methyl, $R^4$, $R^5$, $R^6$ and $R^7$ are hydrogen, and $R^2$ and $R^3$ are as defined below:

| Compound Number | $R^2$ | $R^3$ |
|---|---|---|
| 1.070 | 4-chloro-2,3-difluorophenyl | H |
| 1.071 | 4-chloro-2,5-difluorophenyl | H |
| 1.072 | 4,-chloro-2,6-difluorophenyl | H |
| 1.073 | 2,4-dichloro-3-fluorophenyl | H |
| 1.074 | 2,4-dichloro-5-fluorophenyl | H |
| 1.075 | 2,4-dichloro-6-fluorophenyl | H |
| 1.076 | 2,3,4-trichlorophenyl | H |
| 1.077 | 2,3,5-trichlorophenyl | H |
| 1.078 | 2,3,6-trichlorophenyl | H |
| 1.079 | 2,4,5-trichlorophenyl | H |
| 1.080 | 2,4,6-trichlorophenyl | H |
| 1.081 | 2,3,4-trifluorophenyl | H |
| 1.082 | 2,3,5-trifluorophenyl | H |
| 1.083 | 2,3,6-trifluorophenyl | H |
| 1.084 | 2,4,5-trifluorophenyl | H |
| 1.085 | 2,4,6-trifluorophenyl | H |
| 1.086 | 2-fluoro-4-trifluoromethylphenyl | H |
| 1.087 | 3-fluoro-4-trifluoromethylphenyl | H |
| 1.088 | 2-chloropyridin-5-yl | H |
| 1.089 | 3-chloropyridinyl-5-yl | H |
| 1.090 | 2-methylpyridin-5-yl | H |
| 1.091 | 3-methylpyridinyl-5-yl | H |
| 1.092 | 2-trifluoromethylpyridin-5-yl | H |
| 1.093 | 3-trifluoromethylpyridin-5-yl | H |
| 1.094 | 2-chloro-3-methylpyridin-5-yl | H |
| 1.095 | 2-chloro-4-methylpyridin-5-yl | H |
| 1.096 | 6-chloro-2-methylpyridin-3-yl | H |
| 1.097 | 2,3-dichloropyridin-5-yl | H |
| 1.098 | 2,4-dichloropyridin-5-yl | H |
| 1.099 | 2,6-dichloropyridin-3-yl | H |
| 1.100 | pyrazin-2-yl | H |
| 1.101 | 2-chloropyrazin-5-yl | H |
| 1.102 | 2-bromopyrazin-5-yl | H |
| 1.103 | pyridazin-3-yl | H |
| 1.104 | 6-bromopyridazin-3-yl | H |
| 1.105 | 6-chloropyridazin-3-yl | H |
| 1.106 | pyrimidin-5-yl | H |
| 1.107 | 2-bromopyrimidin-5-yl | H |
| 1.108 | 5-bromopyrimidin-2-yl | H |
| 1.109 | 2-chloropyrimidin-5-yl | H |
| 1.110 | 5-chloropyrimidin-2-yl | H |
| 1.111 | 2-furyl | H |
| 1.112 | 3-furyl | H |
| 1.113 | 2-thienyl | H |
| 1.114 | 3-thienyl | H |
| 1.115 | 4-bromothien-2-yl | H |
| 1.116 | 5-bromothien-2-yl | H |
| 1.117 | 4-chlorothien-2-yl | H |
| 1.118 | 5-chlorothien-2-yl | H |
| 1.119 | pyrazol-1-yl | H |
| 1.120 | 3-chloropyrazol-1-yl | H |
| 1.121 | 4-chloropyrazol-1-yl | H |
| 1.122 | 1-methylpyrazol-4-yl | H |
| 1.123 | 1-methyl-3-trifluoromethylpyrazol-5-yl | H |
| 1.124 | 2-thiazolyl | H |
| 1.125 | 4-methylthiazol-2-yl | H |
| 1.126 | 5-methylthiazol-2-yl | H |
| 1.127 | phenyl | $CH_3$ |
| 1.128 | 2-fluorophenyl | $CH_3$ |
| 1.129 | 3-fluorophenyl | $CH_3$ |
| 1.130 | 4-fluorophenyl | $CH_3$ |
| 1.131 | 2-chlorophenyl | $CH_3$ |
| 1.132 | 3-chlorophenyl | $CH_3$ |

TABLE 1-continued

This table covers 378 compounds of the type (T-1):

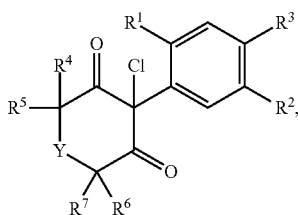

(T-1)

wherein Y is O, $R^1$ is methyl, $R^4$, $R^5$, $R^6$ and $R^7$ are hydrogen, and $R^2$ and $R^3$ are as defined below:

| Compound Number | $R^2$ | $R^3$ |
|---|---|---|
| 1.133 | 4-chlorophenyl | $CH_3$ |
| 1.134 | 2-bromophenyl | $CH_3$ |
| 1.135 | 3-bromophenyl | $CH_3$ |
| 1.136 | 4-bromophenyl | $CH_3$ |
| 1.137 | 4-tert-butyl | $CH_3$ |
| 1.138 | 2-iodophenyl | $CH_3$ |
| 1.139 | 3-iodophenyl | $CH_3$ |
| 1.140 | 4-iodophenyl | $CH_3$ |
| 1.141 | 2-methylphenyl | $CH_3$ |
| 1.142 | 3-methylphenyl | $CH_3$ |
| 1.143 | 4-methylphenyl | $CH_3$ |
| 1.144 | 2-cyanophenyl | $CH_3$ |
| 1.145 | 3-cyanophenyl | $CH_3$ |
| 1.146 | 4-cyanophenyl | $CH_3$ |
| 1.147 | 2-methoxyphenyl | $CH_3$ |
| 1.148 | 3-methoxyphenyl | $CH_3$ |
| 1.149 | 4-methoxyphenyl | $CH_3$ |
| 1.150 | 2-difluoromethoxyphenyl | $CH_3$ |
| 1.151 | 3-difluoromethoxyphenyl | $CH_3$ |
| 1.152 | 4-difluoromethoxyphenyl | $CH_3$ |
| 1.153 | 2-difluoromethylphenyl | $CH_3$ |
| 1.154 | 3-difluoromethylphenyl | $CH_3$ |
| 1.155 | 4-difluoromethylphenyl | $CH_3$ |
| 1.156 | 2-trifluoromethylphenyl | $CH_3$ |
| 1.157 | 3-trifluoromethylphenyl | $CH_3$ |
| 1.158 | 4-trifluoromethylphenyl | $CH_3$ |
| 1.159 | 2-trifluoromethoxyphenyl | $CH_3$ |
| 1.160 | 3-trifluoromethoxyphenyl | $CH_3$ |
| 1.161 | 4-trifluoromethoxyphenyl | $CH_3$ |
| 1.162 | 4-methylthiophenyl | $CH_3$ |
| 1.163 | 4-methylsulfinylphenyl | $CH_3$ |
| 1.164 | 4-methylsulfonylphenyl | $CH_3$ |
| 1.165 | 4-trifluoromethylthiophenyl | $CH_3$ |
| 1.166 | 4-trifluoromethylsulfinylphenyl | $CH_3$ |
| 1.167 | 4-trifluoromethylsulfonylphenyl | $CH_3$ |
| 1.168 | 2,3-difluorophenyl | $CH_3$ |
| 1.169 | 2,4-difluorophenyl | $CH_3$ |
| 1.170 | 2,5-difluorophenyl | $CH_3$ |
| 1.171 | 2,6-difluorophenyl | $CH_3$ |
| 1.172 | 3,4-difluorophenyl | $CH_3$ |
| 1.173 | 3,5-difluorophenyl | $CH_3$ |
| 1.174 | 2,3-dichlorophenyl | $CH_3$ |
| 1.175 | 2,4-dichlorophenyl | $CH_3$ |
| 1.176 | 2,5-dichlorophenyl | $CH_3$ |
| 1.177 | 2,6-dichlorophenyl | $CH_3$ |
| 1.178 | 3,4-dichlorophenyl | $CH_3$ |
| 1.179 | 3,5-dichlorophenyl | $CH_3$ |
| 1.180 | 4-chloro-2-cyanophenyl | $CH_3$ |
| 1.181 | 4-chloro-3-cyanophenyl | $CH_3$ |
| 1.182 | 4-chloro-2-fluorophenyl | $CH_3$ |
| 1.183 | 4-chloro-3-fluorophenyl | $CH_3$ |
| 1.184 | 4-chloro-2-methoxyphenyl | $CH_3$ |
| 1.185 | 4-chloro-3-methoxyphenyl | $CH_3$ |
| 1.186 | 4-chloro-2-methylphenyl | $CH_3$ |
| 1.187 | 4-chloro-3-methylphenyl | $CH_3$ |
| 1.188 | 4-chloro-2-difluoromethoxyphenyl | $CH_3$ |
| 1.189 | 4-chloro-3-difluoromethoxyphenyl | $CH_3$ |
| 1.190 | 4-chloro-2-trifluoromethoxyphenyl | $CH_3$ |
| 1.191 | 4-chloro-3-trifluoromethoxyphenyl | $CH_3$ |
| 1.192 | 4-chloro-2-difluoromethylphenyl | $CH_3$ |
| 1.193 | 4-chloro-3-difluoromethylphenyl | $CH_3$ |
| 1.194 | 4-chloro-2-trifluoromethylphenyl | $CH_3$ |
| 1.195 | 4-chloro-3-trifluoromethylphenyl | $CH_3$ |

TABLE 1-continued

This table covers 378 compounds of the type (T-1):

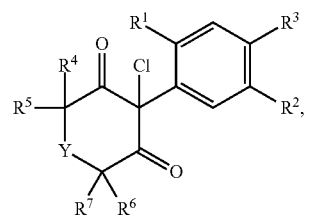

(T-1)

wherein Y is O, $R^1$ is methyl, $R^4$, $R^5$, $R^6$ and $R^7$ are hydrogen, and $R^2$ and $R^3$ are as defined below:

| Compound Number | $R^2$ | $R^3$ |
|---|---|---|
| 1.196 | 4-chloro-2,3-difluorophenyl | $CH_3$ |
| 1.197 | 4-chloro-2,5-difluorophenyl | $CH_3$ |
| 1.198 | 4,-chloro-2,6-difluorophenyl | $CH_3$ |
| 1.199 | 2,4-dichloro-3-fluorophenyl | $CH_3$ |
| 1.200 | 2,4-dichloro-5-fluorophenyl | $CH_3$ |
| 1.201 | 2,4-dichloro-6-fluorophenyl | $CH_3$ |
| 1.202 | 2,3,4-trichlorophenyl | $CH_3$ |
| 1.203 | 2,3,5-trichlorophenyl | $CH_3$ |
| 1.204 | 2,3,6-trichlorophenyl | $CH_3$ |
| 1.205 | 2,4,5-trichlorophenyl | $CH_3$ |
| 1.206 | 2,4,6-trichlorophenyl | $CH_3$ |
| 1.207 | 2,3,4-trifluorophenyl | $CH_3$ |
| 1.208 | 2,3,5-trifluorophenyl | $CH_3$ |
| 1.209 | 2,3,6-trifluorophenyl | $CH_3$ |
| 1.210 | 2,4,5-trifluorophenyl | $CH_3$ |
| 1.211 | 2,4,6-trifluorophenyl | $CH_3$ |
| 1.212 | 2-fluoro-4-trifluoromethylphenyl | $CH_3$ |
| 1.213 | 3-fluoro-4-trifluoromethylphenyl | $CH_3$ |
| 1.214 | 2-chloropyridin-5-yl | $CH_3$ |
| 1.215 | 3-chloropyridinyl-5-yl | $CH_3$ |
| 1.216 | 2-methylpyridin-5-yl | $CH_3$ |
| 1.217 | 3-methylpyridinyl-5-yl | $CH_3$ |
| 1.218 | 2-trifluoromethylpyridin-5-yl | $CH_3$ |
| 1.219 | 3-trifluoromethylpyridin-5-yl | $CH_3$ |
| 1.220 | 2-chloro-3-methylpyridin-5-yl | $CH_3$ |
| 1.221 | 2-chloro-4-methylpyridin-5-yl | $CH_3$ |
| 1.222 | 6-chloro-2-methylpyridin-3-yl | $CH_3$ |
| 1.223 | 2,3-dichloropyridin-5-yl | $CH_3$ |
| 1.224 | 2,4-dichloropyridin-5-yl | $CH_3$ |
| 1.225 | 2,6-dichloropyridin-3-yl | $CH_3$ |
| 1.226 | pyrazin-2-yl | $CH_3$ |
| 1.227 | 2-chloropyrazin-5-yl | $CH_3$ |
| 1.228 | 2-bromopyrazin-5-yl | $CH_3$ |
| 1.229 | pyridazin-3-yl | $CH_3$ |
| 1.230 | 6-bromopyridazin-3-yl | $CH_3$ |
| 1.231 | 6-chloropyridazin-3-yl | $CH_3$ |
| 1.232 | pyrimidin-5-yl | $CH_3$ |
| 1.233 | 2-bromopyrimidin-5-yl | $CH_3$ |
| 1.234 | 5-bromopyrimidin-2-yl | $CH_3$ |
| 1.235 | 2-chloropyrimidin-5-yl | $CH_3$ |
| 1.236 | 5-chloropyrimidin-2-yl | $CH_3$ |
| 1.237 | 2-furyl | $CH_3$ |
| 1.238 | 3-furyl | $CH_3$ |
| 1.239 | 2-thienyl | $CH_3$ |
| 1.240 | 3-thienyl | $CH_3$ |
| 1.241 | 4-bromothien-2-yl | $CH_3$ |
| 1.242 | 5-bromothien-2-yl | $CH_3$ |
| 1.243 | 4-chlorothien-2-yl | $CH_3$ |
| 1.244 | 5-chlorothien-2-yl | $CH_3$ |
| 1.245 | pyrazol-1-yl | $CH_3$ |
| 1.246 | 3-chloropyrazol-1-yl | $CH_3$ |
| 1.247 | 4-chloropyrazol-1-yl | $CH_3$ |
| 1.248 | 1-methylpyrazol-4-yl | $CH_3$ |
| 1.249 | 1-methyl-3-trifluoromethylpyrazol-5-yl | $CH_3$ |
| 1.250 | 2-thiazolyl | $CH_3$ |
| 1.251 | 4-methylthiazol-2-yl | $CH_3$ |
| 1.252 | 5-methylthiazol-2-yl | $CH_3$ |
| 1.253 | phenyl | Cl |
| 1.254 | 2-fluorophenyl | Cl |
| 1.255 | 3-fluorophenyl | Cl |
| 1.256 | 4-fluorophenyl | Cl |
| 1.257 | 2-chlorophenyl | Cl |
| 1.258 | 3-chlorophenyl | Cl |

TABLE 1-continued

This table covers 378 compounds of the type (T-1):

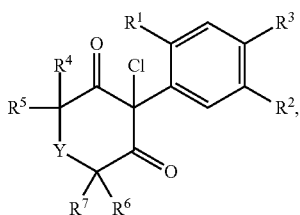

(T-1)

wherein Y is O, $R^1$ is methyl, $R^4$, $R^5$, $R^6$ and $R^7$ are hydrogen, and $R^2$ and $R^3$ are as defined below:

| Compound Number | $R^2$ | $R^3$ |
|---|---|---|
| 1.259 | 4-chlorophenyl | Cl |
| 1.260 | 2-bromophenyl | Cl |
| 1.261 | 3-bromophenyl | Cl |
| 1.262 | 4-bromophenyl | Cl |
| 1.263 | 4-tert-butyl | Cl |
| 1.264 | 2-iodophenyl | Cl |
| 1.265 | 3-iodophenyl | Cl |
| 1.266 | 4-iodophenyl | Cl |
| 1.267 | 2-methylphenyl | Cl |
| 1.268 | 3-methylphenyl | Cl |
| 1.269 | 4-methylphenyl | Cl |
| 1.270 | 2-cyanophenyl | Cl |
| 1.271 | 3-cyanophenyl | Cl |
| 1.272 | 4-cyanophenyl | Cl |
| 1.273 | 2-methoxyphenyl | Cl |
| 1.274 | 3-methoxyphenyl | Cl |
| 1.275 | 4-methoxyphenyl | Cl |
| 1.276 | 2-difluoromethoxyphenyl | Cl |
| 1.277 | 3-difluoromethoxyphenyl | Cl |
| 1.278 | 4-difluoromethoxyphenyl | Cl |
| 1.279 | 2-difluoromethylphenyl | Cl |
| 1.280 | 3-difluoromethylphenyl | Cl |
| 1.281 | 4-difluoromethylphenyl | Cl |
| 1.282 | 2-trifluoromethylphenyl | Cl |
| 1.283 | 3-trifluoromethylphenyl | Cl |
| 1.284 | 4-trifluoromethylphenyl | Cl |
| 1.285 | 2-trifluoromethoxyphenyl | Cl |
| 1.286 | 3-trifluoromethoxyphenyl | Cl |
| 1.287 | 4-trifluoromethoxyphenyl | Cl |
| 1.288 | 4-methylthiophenyl | Cl |
| 1.289 | 4-methylsulfinylphenyl | Cl |
| 1.290 | 4-methylsulfonylphenyl | Cl |
| 1.291 | 4-trifluoromethylthiophenyl | Cl |
| 1.292 | 4-trifluoromethylsulfinylphenyl | Cl |
| 1.293 | 4-trifluoromethylsulfonylphenyl | Cl |
| 1.294 | 2,3-difluorophenyl | Cl |
| 1.295 | 2,4-difluorophenyl | Cl |
| 1.296 | 2,5-difluorophenyl | Cl |
| 1.297 | 2,6-difluorophenyl | Cl |
| 1.298 | 3,4-difluorophenyl | Cl |
| 1.299 | 3,5-difluorophenyl | Cl |
| 1.300 | 2,3-dichlorophenyl | Cl |
| 1.301 | 2,4-dichlorophenyl | Cl |
| 1.302 | 2,5-dichlorophenyl | Cl |
| 1.303 | 2,6-dichlorophenyl | Cl |
| 1.304 | 3,4-dichlorophenyl | Cl |
| 1.305 | 3,5-dichlorophenyl | Cl |
| 1.306 | 4-chloro-2-cyanophenyl | Cl |
| 1.307 | 4-chloro-3-cyanophenyl | Cl |
| 1.308 | 4-chloro-2-fluorophenyl | Cl |
| 1.309 | 4-chloro-3-fluorophenyl | Cl |
| 1.310 | 4-chloro-2-methoxyphenyl | Cl |
| 1.311 | 4-chloro-3-methoxyphenyl | Cl |
| 1.312 | 4-chloro-2-methylphenyl | Cl |
| 1.313 | 4-chloro-3-methylphenyl | Cl |
| 1.314 | 4-chloro-2-difluoromethoxyphenyl | Cl |
| 1.315 | 4-chloro-3-difluoromethoxyphenyl | Cl |
| 1.316 | 4-chloro-2-trifluoromethoxyphenyl | Cl |
| 1.317 | 4-chloro-3-trifluoromethoxyphenyl | Cl |
| 1.318 | 4-chloro-2-difluoromethylphenyl | Cl |
| 1.319 | 4-chloro-3-difluoromethylphenyl | Cl |
| 1.320 | 4-chloro-2-trifluoromethylphenyl | Cl |
| 1.321 | 4-chloro-3-trifluoromethylphenyl | Cl |
| 1.322 | 4-chloro-2,3-difluorophenyl | Cl |
| 1.323 | 4-chloro-2,5-difluorophenyl | Cl |
| 1.324 | 4,-chloro-2,6-difluorophenyl | Cl |
| 1.325 | 2,4-dichloro-3-fluorophenyl | Cl |
| 1.326 | 2,4-dichloro-5-fluorophenyl | Cl |
| 1.327 | 2,4-dichloro-6-fluorophenyl | Cl |
| 1.328 | 2,3,4-trichlorophenyl | Cl |
| 1.329 | 2,3,5-trichlorophenyl | Cl |
| 1.330 | 2,3,6-trichlorophenyl | Cl |
| 1.331 | 2,4,5-trichlorophenyl | Cl |
| 1.332 | 2,4,6-trichlorophenyl | Cl |
| 1.333 | 2,3,4-trifluorophenyl | Cl |
| 1.334 | 2,3,5-trifluorophenyl | Cl |
| 1.335 | 2,3,6-trifluorophenyl | Cl |
| 1.336 | 2,4,5-trifluorophenyl | Cl |
| 1.337 | 2,4,6-trifluorophenyl | Cl |
| 1.338 | 2-fluoro-4-trifluoromethylphenyl | Cl |
| 1.339 | 3-fluoro-4-trifluoromethylphenyl | Cl |
| 1.340 | 2-chloropyridin-5-yl | Cl |
| 1.341 | 3-chloropyridinyl-5-yl | Cl |
| 1.342 | 2-methylpyridin-5-yl | Cl |
| 1.343 | 3-methylpyridinyl-5-yl | Cl |
| 1.344 | 2-trifluoromethylpyridin-5-yl | Cl |
| 1.345 | 3-trifluoromethylpyridin-5-yl | Cl |
| 1.346 | 2-chloro-3-methylpyridin-5-yl | Cl |
| 1.347 | 2-chloro-4-methylpyridin-5-yl | Cl |
| 1.348 | 6-chloro-2-methylpyridin-3-yl | Cl |
| 1.349 | 2,3-dichloropyridin-5-yl | Cl |
| 1.350 | 2,4-dichloropyridin-5-yl | Cl |
| 1.351 | 2,6-dichloropyridin-3-yl | Cl |
| 1.352 | pyrazin-2-yl | Cl |
| 1.353 | 2-chloropyrazin-5-yl | Cl |
| 1.354 | 2-bromopyrazin-5-yl | Cl |
| 1.355 | pyridazin-3-yl | Cl |
| 1.356 | 6-bromopyridazin-3-yl | Cl |
| 1.357 | 6-chloropyridazin-3-yl | Cl |
| 1.358 | pyrimidin-5-yl | Cl |
| 1.359 | 2-bromopyrimidin-5-yl | Cl |
| 1.360 | 5-bromopyrimidin-2-yl | Cl |
| 1.361 | 2-chloropyrimidin-5-yl | Cl |
| 1.362 | 5-chloropyrimidin-2-yl | Cl |
| 1.363 | 2-furyl | Cl |
| 1.364 | 3-furyl | Cl |
| 1.365 | 2-thienyl | Cl |
| 1.366 | 3-thienyl | Cl |
| 1.367 | 4-bromothien-2-yl | Cl |
| 1.368 | 5-bromothien-2-yl | Cl |
| 1.369 | 4-chlorothien-2-yl | Cl |
| 1.370 | 5-chlorothien-2-yl | Cl |
| 1.371 | pyrazol-1-yl | Cl |
| 1.372 | 3-chloropyrazol-1-yl | Cl |
| 1.373 | 4-chloropyrazol-1-yl | Cl |
| 1.374 | 1-methylpyrazol-4-yl | Cl |
| 1.375 | 1-methyl-3-trifluoromethylpyrazol-5-yl | Cl |
| 1.376 | 2-thiazolyl | Cl |
| 1.377 | 4-methylthiazol-2-yl | Cl |
| 1.378 | 5-methylthiazol-2-yl | Cl |

Table 2:

This table covers 378 compounds of the type (T-1), wherein Y is O, $R^1$ is ethyl, $R^4$, $R^5$, $R^6$ and $R^7$ are hydrogen, and $R^2$ and $R^3$ are as defined in Table 1.

Table 3:
This table covers 378 compounds of the type (T-1), wherein Y is O, $R^1$ is chlorine, $R^4$, $R^5$, $R^6$ and $R^7$ are hydrogen, and $R^2$ and $R^3$ are as defined in Table 1.

Table 4:
This table covers 378 compounds of the type (T-1), wherein Y is O, $R^1$ is methyl, $R^4$ is methyl, $R^5$, $R^6$ and $R^7$ are hydrogen, and $R^2$ and $R^3$ are as defined in Table 1.

Table 5:
This table covers 378 compounds of the type (T-1), wherein Y is O, $R^1$ is ethyl, $R^4$ is methyl, $R^5$, $R^6$ and $R^7$ are hydrogen, and $R^2$ and $R^3$ are as defined in Table 1.

Table 6:
This table covers 378 compounds of the type (T-1), wherein Y is O, $R^1$ is chlorine, $R^4$ is methyl, $R^5$, $R^6$ and $R^7$ are hydrogen, G is hydrogen and $R^2$ and $R^3$ are as defined in Table 1.

Table 7:
This table covers 378 compounds of the type (T-1), wherein Y is O, $R^1$ is methyl, $R^4$ and $R^5$ are methyl, $R^6$ and $R^7$ are hydrogen, and $R^2$ and $R^3$ are as defined in Table 1.

Table 8:
This table covers 378 compounds of the type (T-1), wherein Y is O, $R^1$ is ethyl, $R^4$ and $R^5$ are methyl, $R^6$ and $R^7$ are hydrogen, and $R^2$ and $R^3$ are as defined in Table 1.

Table 9:
This table covers 378 compounds of the type (T-1), wherein Y is O, $R^1$ is chlorine, $R^4$ and $R^5$ are methyl, $R^6$ and $R^7$ are hydrogen, and $R^2$ and $R^3$ are as defined in Table 1.

Table 10:
This table covers 378 compounds of the type (T-1), wherein Y is O, $R^1$ is methyl, $R^4$ and $R^6$ are methyl, $R^5$ and $R^7$ are hydrogen, G is hydrogen and $R^2$ and $R^3$ are as defined in Table 1.

Table 11:
This table covers 378 compounds of the type (T-1), wherein Y is O, $R^1$ is ethyl, $R^4$ and $R^6$ are methyl, $R^5$ and $R^7$ are hydrogen, and $R^2$ and $R^3$ are as defined in Table 1.

Table 12:
This table covers 378 compounds of the type (T-1), wherein Y is O, $R^1$ is chlorine, $R^4$ and $R^6$ are methyl, $R^5$ and $R^7$ are hydrogen, and $R^2$ and $R^3$ are as defined in Table 1.

Table 13:
This table covers 378 compounds of the type (T-1), wherein Y is O, $R^1$ is methyl, $R^4$, $R^5$ and $R^6$ are methyl, $R^7$ is hydrogen, and $R^2$ and $R^3$ are as defined in Table 1.

Table 14:
This table covers 378 compounds of the type (T-1), wherein Y is O, $R^1$ is ethyl, $R^4$, $R^5$ and $R^6$ are methyl, $R^7$ is hydrogen, and $R^2$ and $R^3$ are as defined in Table 1.

Table 15:
This table covers 378 compounds of the type (T-1), wherein Y is O, $R^1$ is chlorine, $R^4$, $R^5$ and $R^6$ are methyl, $R^7$ is hydrogen, and $R^2$ and $R^3$ are as defined in Table 1.

Table 16:
This table covers 378 compounds of the type (T-1), wherein Y is O, $R^1$ is methyl, $R^4$, $R^5$, $R^6$ and $R^7$ are methyl, and $R^2$ and $R^3$ are as defined in Table 1.

Table 17:
This table covers 378 compounds of the type (T-1), wherein Y is O, $R^1$ is ethyl, $R^4$, $R^5$, $R^6$ and are methyl, and $R^2$ and $R^3$ are as defined in Table 1.

Table 18:
This table covers 378 compounds of the type (T-1), wherein Y is O, $R^1$ is chlorine, $R^4$, $R^5$, $R^6$ and $R^7$ are methyl, and $R^2$ and $R^3$ are as defined in Table 1.

Table 19:
This table covers 378 compounds of the type (T-1), wherein Y is O, $R^1$ is methyl, $R^4$, $R^5$ and $R^6$ are methyl, $R^7$ is methoxymethyl, and $R^2$ and $R^3$ are as defined in Table 1.

Table 20:
This table covers 378 compounds of the type (T-1), wherein Y is O, $R^1$ is ethyl, $R^4$, $R^5$ and $R^6$ are methyl, $R^7$ is methoxymethyl, and $R^2$ and $R^3$ are as defined in Table 1.

Table 21:
This table covers 378 compounds of the type (T-1), wherein Y is O, $R^1$ is chlorine, $R^4$, $R^5$ and $R^6$ are methyl, $R^7$ is methoxymethyl, and $R^2$ and $R^3$ are as defined in Table 1.

Table 22:
This table covers 378 compounds of the type (T-1), wherein Y is S, $R^1$ is methyl, $R^4$, $R^5$, $R^6$ and $R^7$ are hydrogen, and $R^2$ and $R^3$ are as defined in Table 1.

Table 23:
This table covers 378 compounds of the type (T-1), wherein Y is S, $R^1$ is ethyl, $R^4$, $R^5$, $R^6$ and $R^7$ are hydrogen, and $R^2$ and $R^3$ are as defined in Table 1.

Table 24:
This table covers 378 compounds of the type (T-1), wherein Y is S, $R^1$ is chlorine, $R^4$, $R^5$, $R^6$ and $R^7$ are hydrogen, and $R^2$ and $R^3$ are as defined in Table 1.

Table 25:
This table covers 378 compounds of the type (T-1), wherein Y is S, $R^1$ is methyl, $R^4$ is methyl, $R^5$, $R^6$ and $R^7$ are hydrogen, and $R^2$ and $R^3$ are as defined in Table 1.

Table 26:
This table covers 378 compounds of the type (T-1), wherein Y is S, $R^1$ is ethyl, $R^4$ is methyl, $R^5$, $R^6$ and $R^7$ are hydrogen, and $R^2$ and $R^3$ are as defined in Table 1.

Table 27:
This table covers 378 compounds of the type (T-1), wherein Y is S, $R^1$ is chlorine, $R^4$ is methyl, $R^5$, $R^6$ and $R^7$ are hydrogen, and $R^2$ and $R^3$ are as defined in Table 1.

Table 28:
This table covers 378 compounds of the type (T-1), wherein Y is S, $R^1$ is methyl, $R^4$ and $R^5$ are methyl, $R^6$ and $R^7$ are hydrogen, and $R^2$ and $R^3$ are as defined in Table 1.

Table 29:
This table covers 378 compounds of the type (T-1), wherein Y is S, $R^1$ is ethyl, $R^4$ and $R^5$ are methyl, $R^6$ and $R^7$ are hydrogen, and $R^2$ and $R^3$ are as defined in Table 1.

Table 30:
This table covers 378 compounds of the type (T-1), wherein Y is S, $R^1$ is chlorine, $R^4$ and $R^5$ are methyl, $R^6$ and $R^7$ are hydrogen, and $R^2$ and $R^3$ are as defined in Table 1.

Table 31:
This table covers 378 compounds of the type (T-1), wherein Y is S, $R^1$ is methyl, $R^4$ and $R^6$ are methyl, $R^5$ and $R^7$ are hydrogen, and $R^2$ and $R^3$ are as defined in Table 1.

Table 32:
This table covers 378 compounds of the type (T-1), wherein Y is S, $R^1$ is ethyl, $R^4$ and $R^6$ are methyl, $R^5$ and $R^7$ are hydrogen, and $R^2$ and $R^3$ are as defined in Table 1.

Table 33:
This table covers 378 compounds of the type (T-1), wherein Y is S, $R^1$ is chlorine, $R^4$ and $R^6$ are methyl, $R^5$ and $R^7$ are hydrogen, and $R^2$ and $R^3$ are as defined in Table 1.

Table 34:
This table covers 378 compounds of the type (T-1), wherein Y is S, $R^1$ is methyl, $R^4$, $R^5$ and $R^6$ are methyl, $R^7$ is hydrogen, and $R^2$ and $R^3$ are as defined in Table 1.

Table 35:
This table covers 378 compounds of the type (T-1), wherein Y is S, $R^1$ is ethyl, $R^4$, $R^5$ and $R^6$ are methyl, $R^7$ is hydrogen, and $R^2$ and $R^3$ are as defined in Table 1.

Table 36:
This table covers 378 compounds of the type (T-1), wherein Y is S, $R^1$ is chlorine, $R^4$, $R^5$ and $R^6$ are methyl, $R^7$ is hydrogen, and $R^2$ and $R^3$ are as defined in Table 1.

Table 37:
This table covers 378 compounds of the type (T-1), wherein Y is S, $R^1$ is methyl, $R^4$, $R^5$, $R^6$ and $R^7$ are methyl, and $R^2$ and $R^3$ are as defined in Table 1.

Table 38:
This table covers 378 compounds of the type (T-1), wherein Y is S, $R^1$ is ethyl, $R^4$, $R^5$, $R^6$ and are methyl, and $R^2$ and $R^3$ are as defined in Table 1.

Table 39:
This table covers 378 compounds of the type (T-1), wherein Y is S, $R^1$ is chlorine, $R^4$, $R^5$, $R^6$ and $R^7$ are methyl, and $R^2$ and $R^3$ are as defined in Table 1.

Table 40:
This table covers 378 compounds of the type (T-1), wherein Y is S=O, $R^1$ is methyl, $R^4$, $R^5$, $R^6$ and $R^7$ are hydrogen, and $R^2$ and $R^3$ are as defined in Table 1.

Table 41:
This table covers 378 compounds of the type (T-1), wherein Y is S=O, $R^1$ is ethyl, $R^4$, $R^5$, $R^6$ and $R^7$ are hydrogen, and $R^2$ and $R^3$ are as defined in Table 1.

Table 42:
This table covers 378 compounds of the type (T-1), wherein Y is S=O, $R^1$ is chlorine, $R^4$, $R^5$, $R^6$ and $R^7$ are hydrogen, and $R^2$ and $R^3$ are as defined in Table 1.

Table 43:
This table covers 378 compounds of the type (T-1), wherein Y is S=O, $R^1$ is methyl, $R^4$ is methyl, $R^5$, $R^6$ and $R^7$ are hydrogen, and $R^2$ and $R^3$ are as defined in Table 1.

Table 44
This table covers 378 compounds of the type (T-1), wherein Y is S=O, $R^1$ is ethyl, $R^4$ is methyl, $R^5$, $R^6$ and $R^7$ are hydrogen, and $R^2$ and $R^3$ are as defined in Table 1.

Table 45:
This table covers 378 compounds of the type (T-1), wherein Y is S=O, $R^1$ is chlorine, $R^4$ is methyl, $R^5$, $R^6$ and $R^7$ are hydrogen, and $R^2$ and $R^3$ are as defined in Table 1.

Table 46:
This table covers 378 compounds of the type (T-1), wherein Y is S=O, $R^1$ is methyl, $R^4$ and $R^5$ are methyl, $R^6$ and $R^7$ are hydrogen, and $R^2$ and $R^3$ are as defined in Table 1.

Table 47:
This table covers 378 compounds of the type (T-1), wherein Y is S=O, $R^1$ is ethyl, $R^4$ and $R^5$ are methyl, $R^6$ and $R^7$ are hydrogen, and $R^2$ and $R^3$ are as defined in Table 1.

Table 48:
This table covers 378 compounds of the type (T-1), wherein Y is S=O, $R^1$ is chlorine, $R^4$ and $R^5$ are methyl, $R^6$ and $R^7$ are hydrogen, and $R^2$ and $R^3$ are as defined in Table 1.

Table 49:
This table covers 378 compounds of the type (T-1), wherein Y is S=O, $R^1$ is methyl, $R^4$ and $R^6$ are methyl, $R^5$ and $R^7$ are hydrogen, and $R^2$ and $R^3$ are as defined in Table 1.

Table 50:
This table covers 378 compounds of the type (T-1), wherein Y is S=O, $R^1$ is ethyl, $R^4$ and $R^6$ are methyl, $R^5$ and $R^7$ are hydrogen, and $R^2$ and $R^3$ are as defined in Table 1.

Table 51:
This table covers 378 compounds of the type (T-1), wherein Y is S=O, $R^1$ is chlorine, $R^4$ and $R^6$ are methyl, $R^5$ and $R^7$ are hydrogen, and $R^2$ and $R^3$ are as defined in Table 1.

Table 52:
This table covers 378 compounds of the type (T-1), wherein Y is S=O, $R^1$ is methyl, $R^4$, $R^5$ and $R^6$ are methyl, $R^7$ is hydrogen, and $R^2$ and $R^3$ are as defined in Table 1.

Table 53:
This table covers 378 compounds of the type (T-1), wherein Y is S=O, $R^1$ is ethyl, $R^4$, $R^5$ and $R^6$ are methyl, $R^7$ is hydrogen, and $R^2$ and $R^3$ are as defined in Table 1.

Table 54:
This table covers 378 compounds of the type (T-1), wherein Y is S=O, $R^1$ is chlorine, $R^4$, $R^5$ and $R^6$ are methyl, $R^7$ is hydrogen, and $R^2$ and $R^3$ are as defined in Table 1.

Table 55:
This table covers 378 compounds of the type (T-1), wherein Y is S=O, $R^1$ is methyl, $R^4$, $R^5$, $R^6$ and $R^7$ are methyl, and $R^2$ and $R^3$ are as defined in Table 1.

Table 56:
This table covers 378 compounds of the type (T-1), wherein Y is S=O, $R^1$ is ethyl, $R^4$, $R^5$, $R^6$ and $R^7$ are methyl, and $R^2$ and $R^3$ are as defined in Table 1.

Table 57:
This table covers 378 compounds of the type (T-1), wherein Y is S=O, $R^1$ is chlorine, $R^4$, $R^5$, $R^6$ and $R^7$ are methyl, and $R^2$ and $R^3$ are as defined in Table 1.

Table 58:
This table covers 378 compounds of the type (T-1), wherein Y is $S(=O)_2$, $R^1$ is methyl, $R^4$, $R^5$, $R^6$ and $R^7$ are hydrogen, and $R^2$ and $R^3$ are as defined in Table 1.

Table 59:
This table covers 378 compounds of the type (T-1), wherein Y is $S(=O)_2$, $R^1$ is ethyl, $R^4$, $R^5$, $R^6$ and $R^7$ are hydrogen, and $R^2$ and $R^3$ are as defined in Table 1.

Table 60:
This table covers 378 compounds of the type (T-1), wherein Y is $S(=O)_2$, $R^1$ is chlorine, $R^4$, $R^5$, $R^6$ and $R^7$ are hydrogen, and $R^2$ and $R^3$ are as defined in Table 1.

Table 61:
This table covers 378 compounds of the type (T-1), wherein Y is $S(=O)_2$, $R^1$ is methyl, $R^4$ is methyl, $R^5$, $R^6$ and $R^7$ are hydrogen, and $R^2$ and $R^3$ are as defined in Table 1.

Table 62:
This table covers 378 compounds of the type (T-1), wherein Y is $S(=O)_2$, $R^1$ is ethyl, $R^4$ is methyl, $R^5$, $R^6$ and $R^7$ are hydrogen, and $R^2$ and $R^3$ are as defined in Table 1.

Table 63:
This table covers 378 compounds of the type (T-1), wherein Y is $S(=O)_2$, $R^1$ is chlorine, $R^4$ is methyl, $R^5$, $R^6$ and $R^7$ are hydrogen, and $R^2$ and $R^3$ are as defined in Table 1.

Table 64:
This table covers 378 compounds of the type (T-1), wherein Y is $S(=O)_2$, $R^1$ is methyl, $R^4$ and $R^5$ are methyl, $R^6$ and $R^7$ are hydrogen, and $R^2$ and $R^3$ are as defined in Table 1.

Table 65:
This table covers 378 compounds of the type (T-1), wherein Y is $S(=O)_2$, $R^1$ is ethyl, $R^4$ and $R^5$ are methyl, $R^6$ and $R^7$ are hydrogen, and $R^2$ and $R^3$ are as defined in Table 1.

Table 66:
This table covers 378 compounds of the type (T-1), wherein Y is $S(=O)_2$, $R^1$ is chlorine, $R^4$ and $R^5$ are methyl, $R^6$ and $R^7$ are hydrogen, and $R^2$ and $R^3$ are as defined in Table 1.

Table 67:
This table covers 378 compounds of the type (T-1), wherein Y is S(=O)$_2$, R$^1$ is methyl, R$^4$ and R$^6$ are methyl, R$^5$ and R$^7$ are hydrogen, and R$^2$ and R$^3$ are as defined in Table 1.

Table 68:
This table covers 378 compounds of the type (T-1), wherein Y is S(=O)$_2$, R$^1$ is ethyl, R$^4$ and R$^6$ are methyl, R$^5$ and R$^7$ are hydrogen, and R$^2$ and R$^3$ are as defined in Table 1.

Table 69:
This table covers 378 compounds of the type (T-1), wherein Y is S(=O)$_2$, R$^1$ is chlorine, R$^4$ and R$^6$ are methyl, R$^5$ and R$^7$ are hydrogen, and R$^2$ and R$^3$ are as defined in Table 1.

Table 70:
This table covers 378 compounds of the type (T-1), wherein Y is S(=O)$_2$, R$^1$ is methyl, R$^4$, R$^5$ and R$^6$ are methyl, R$^7$ is hydrogen, and R$^2$ and R$^3$ are as defined in Table 1.

Table 71:
This table covers 378 compounds of the type (T-1), wherein Y is S(=O)$_2$, R$^1$ is ethyl, R$^4$, R$^5$ and R$^6$ are methyl, R$^7$ is hydrogen, and R$^2$ and R$^3$ are as defined in Table 1.

Table 72:
This table covers 378 compounds of the type (T-1), wherein Y is S(=O)$_2$, R$^1$ is chlorine, R$^4$, R$^5$ and R$^6$ are methyl, R$^7$ is hydrogen, and R$^2$ and R$^3$ are as defined in Table 1.

Table 73:
This table covers 378 compounds of the type (T-1), wherein Y is S(=O)$_2$, R$^1$ is methyl, R$^4$, R$^5$, R$^6$ and R$^7$ are methyl, and R$^2$ and R$^3$ are as defined in Table 1.

Table 74:
This table covers 378 compounds of the type (T-1), wherein Y is S(=O)$_2$, R$^1$ is ethyl, R$^4$, R$^5$, R$^6$ and R$^7$ are methyl, and R$^2$ and R$^3$ are as defined in Table 1.

Table 75:
This table covers 378 compounds of the type (T-1), wherein Y is S(=O)$_2$, R$^1$ is chlorine, R$^4$, R$^5$, R$^6$ and R$^7$ are methyl, and R$^2$ and R$^3$ are as defined in Table 1.

Table 76:
This table covers 378 compounds of the type (T-1), wherein Y is C=O, R$^1$ is methyl, R$^4$ and R$^5$ are methyl, R$^6$ and R$^7$ are hydrogen, and R$^2$ and R$^3$ are as defined in Table 1.

Table 77:
This table covers 378 compounds of the type (T-1), wherein Y is C=O, R$^1$ is ethyl, R$^4$ and R$^5$ are methyl, R$^6$ and R$^7$ are hydrogen, and R$^2$ and R$^3$ are as defined in Table 1.

Table 78:
This table covers 378 compounds of the type (T-1), wherein Y is C=O, R$^1$ is ethyl, R$^4$ and R$^5$ are methyl, R$^6$ and R$^7$ are hydrogen, and R$^2$ and R$^3$ are as defined in Table 1.

Table 79:
This table covers 378 compounds of the type (T-1), wherein Y is C=O, R$^1$ is methyl, R$^4$, R$^5$ and R$^6$ are methyl, R$^7$ is hydrogen, and R$^2$ and R$^3$ are as defined in Table 1.

Table 80:
This table covers 378 compounds of the type (T-1), wherein Y is C=O, R$^1$ is ethyl, R$^4$, R$^5$ and R$^6$ are methyl, R$^7$ is hydrogen, and R$^2$ and R$^3$ are as defined in Table 1.

Table 81:
This table covers 378 compounds of the type (T-1), wherein Y is C=O, R$^1$ is chlorine, R$^4$, R$^5$ and R$^6$ are methyl, R$^7$ is hydrogen, and R$^2$ and R$^3$ are as defined in Table 1.

Table 82:
This table covers 378 compounds of the type (T-1), wherein Y is C=O, R$^1$ is methyl, R$^4$, R$^5$, R$^6$ and R$^7$ are methyl, and R$^2$ and R$^3$ are as defined in Table 1.

Table 83:
This table covers 378 compounds of the type (T-1), wherein Y is C=O, R$^1$ is ethyl, R$^4$, R$^5$, R$^6$ and R$^7$ are methyl, and R$^2$ and R$^3$ are as defined in Table 1.

Table 84:
This table covers 378 compounds of the type (T-1), wherein Y is C=O, R$^1$ is chlorine, R$^4$, R$^5$, R$^6$ and R$^7$ are methyl, and R$^2$ and R$^3$ are as defined in Table 1.

TABLE 85

This table covers 378 compounds of the type (T-2):

(T-2)

wherein Y is O, R$^1$ is methyl, R$^4$, R$^5$, R$^6$ and R$^7$ are hydrogen, and R$^2$ and R$^3$ are as defined below:

Table 86:
This table covers 378 compounds of the type (T-2), wherein Y is O, R$^1$ is ethyl, R$^4$, R$^5$, R$^6$ and R$^7$ are hydrogen, and R$^2$ and R$^3$ are as defined in Table 1.

Table 87:
This table covers 378 compounds of the type (T-2), wherein Y is O, R$^1$ is chlorine, R$^4$, R$^5$, R$^6$ and R$^7$ are hydrogen, and R$^2$ and R$^3$ are as defined in Table 1.

Table 88:
This table covers 378 compounds of the type (T-2), wherein Y is O, R$^1$ is methyl, R$^4$ is methyl, R$^5$, R$^6$ and R$^7$ are hydrogen, and R$^2$ and R$^3$ are as defined in Table 1.

Table 89:
This table covers 378 compounds of the type (T-2), wherein Y is O, R$^1$ is ethyl, R$^4$ is methyl, R$^5$, R$^6$ and R$^7$ are hydrogen, and R$^2$ and R$^3$ are as defined in Table 1.

Table 90:
This table covers 378 compounds of the type (T-2), wherein Y is O, R$^1$ is chlorine, R$^4$ is methyl, R$^5$, R$^6$ and R$^7$ are hydrogen, G is hydrogen and R$^2$ and R$^3$ are as defined in Table 1.

Table 91:
This table covers 378 compounds of the type (T-2), wherein Y is O, R$^1$ is methyl, R$^4$ and R$^5$ are methyl, R$^6$ and R$^7$ are hydrogen, and R$^2$ and R$^3$ are as defined in Table 1.

Table 92:
This table covers 378 compounds of the type (T-2), wherein Y is O, R$^1$ is ethyl, R$^4$ and R$^5$ are methyl, R$^6$ and R$^7$ are hydrogen, and R$^2$ and R$^3$ are as defined in Table 1.

Table 93:
This table covers 378 compounds of the type (T-2), wherein Y is O, R$^1$ is chlorine, R$^4$ and R$^5$ are methyl, R$^6$ and R$^7$ are hydrogen, and R$^2$ and R$^3$ are as defined in Table 1.

Table 94:
This table covers 378 compounds of the type (T-2), wherein Y is O, R$^1$ is methyl, R$^4$ and R$^6$ are methyl, R$^5$ and R$^7$ are hydrogen, G is hydrogen and R$^2$ and R$^3$ are as defined in Table 1.

Table 95:
This table covers 378 compounds of the type (T-2), wherein Y is O, R$^1$ is ethyl, R$^4$ and R$^6$ are methyl, R$^5$ and R$^7$ are hydrogen, and R$^2$ and R$^3$ are as defined in Table 1.

Table 96:
This table covers 378 compounds of the type (T-2), wherein Y is O, $R^1$ is chlorine, $R^4$ and $R^6$ are methyl, $R^5$ and $R^7$ are hydrogen, and $R^2$ and $R^3$ are as defined in Table 1.

Table 97:
This table covers 378 compounds of the type (T-2), wherein Y is O, $R^1$ is methyl, $R^4$, $R^5$ and $R^6$ are methyl, $R^7$ is hydrogen, and $R^2$ and $R^3$ are as defined in Table 1.

Table 98:
This table covers 378 compounds of the type (T-2), wherein Y is O, $R^1$ is ethyl, $R^4$, $R^5$ and $R^6$ are methyl, $R^7$ is hydrogen, and $R^2$ and $R^3$ are as defined in Table 1.

Table 99:
This table covers 378 compounds of the type (T-2), wherein Y is O, $R^1$ is chlorine, $R^4$, $R^5$ and $R^6$ are methyl, $R^7$ is hydrogen, and $R^2$ and $R^3$ are as defined in Table 1.

Table 100:
This table covers 378 compounds of the type (T-2), wherein Y is O, $R^1$ is methyl, $R^4$, $R^5$, $R^6$ and $R^7$ are methyl, and $R^2$ and $R^3$ are as defined in Table 1.

Table 101:
This table covers 378 compounds of the type (T-2), wherein Y is O, $R^1$ is ethyl, $R^4$, $R^5$, $R^6$ and are methyl, and $R^2$ and $R^3$ are as defined in Table 1.

Table 102:
This table covers 378 compounds of the type (T-2), wherein Y is O, $R^1$ is chlorine, $R^4$, $R^5$, $R^6$ and $R^7$ are methyl, and $R^2$ and $R^3$ are as defined in Table 1.

Table 103:
This table covers 378 compounds of the type (T-2), wherein Y is O, $R^1$ is methyl, $R^4$, $R^5$ and $R^6$ are methyl, $R^7$ is methoxymethyl, and $R^2$ and $R^3$ are as defined in Table 1.

Table 104:
This table covers 378 compounds of the type (T-2), wherein Y is O, $R^1$ is ethyl, $R^4$, $R^5$ and $R^6$ are methyl, $R^7$ is methoxymethyl, and $R^2$ and $R^3$ are as defined in Table 1.

Table 105:
This table covers 378 compounds of the type (T-2), wherein Y is O, $R^1$ is chlorine, $R^4$, $R^5$ and $R^6$ are methyl, $R^7$ is methoxymethyl, and $R^2$ and $R^3$ are as defined in Table 1.

Table 106:
This table covers 378 compounds of the type (T-2), wherein Y is S, $R^1$ is methyl, $R^4$, $R^5$, $R^6$ and $R^7$ are hydrogen, and $R^2$ and $R^3$ are as defined in Table 1.

Table 107:
This table covers 378 compounds of the type (T-2), wherein Y is S, $R^1$ is ethyl, $R^4$, $R^5$, $R^6$ and $R^7$ are hydrogen, and $R^2$ and $R^3$ are as defined in Table 1.

Table 108:
This table covers 378 compounds of the type (T-2), wherein Y is S, $R^1$ is chlorine, $R^4$, $R^5$, $R^6$ and $R^7$ are hydrogen, and $R^2$ and $R^3$ are as defined in Table 1.

Table 109:
This table covers 378 compounds of the type (T-2), wherein Y is S, $R^1$ is methyl, $R^4$ is methyl, $R^5$, $R^6$ and $R^7$ are hydrogen, and $R^2$ and $R^3$ are as defined in Table 1.

Table 110:
This table covers 378 compounds of the type (T-2), wherein Y is S, $R^1$ is ethyl, $R^4$ is methyl, $R^5$, $R^6$ and $R^7$ are hydrogen, and $R^2$ and $R^3$ are as defined in Table 1.

Table 111:
This table covers 378 compounds of the type (T-2), wherein Y is S, $R^1$ is chlorine, $R^4$ is methyl, $R^5$, $R^6$ and $R^7$ are hydrogen, and $R^2$ and $R^3$ are as defined in Table 1.

Table 112:
This table covers 378 compounds of the type (T-2), wherein Y is S, $R^1$ is methyl, $R^4$ and $R^5$ are methyl, $R^6$ and $R^7$ are hydrogen, and $R^2$ and $R^3$ are as defined in Table 1.

Table 113:
This table covers 378 compounds of the type (T-2), wherein Y is S, $R^1$ is ethyl, $R^4$ and $R^5$ are methyl, $R^6$ and $R^7$ are hydrogen, and $R^2$ and $R^3$ are as defined in Table 1.

Table 114:
This table covers 378 compounds of the type (T-2), wherein Y is S, $R^1$ is chlorine, $R^4$ and $R^5$ are methyl, $R^6$ and $R^7$ are hydrogen, and $R^2$ and $R^3$ are as defined in Table 1.

Table 115:
This table covers 378 compounds of the type (T-2), wherein Y is S, $R^1$ is methyl, $R^4$ and $R^6$ are methyl, $R^5$ and $R^7$ are hydrogen, and $R^2$ and $R^3$ are as defined in Table 1.

Table 116:
This table covers 378 compounds of the type (T-2), wherein Y is S, $R^1$ is ethyl, $R^4$ and $R^6$ are methyl, $R^5$ and $R^7$ are hydrogen, and $R^2$ and $R^3$ are as defined in Table 1.

Table 117:
This table covers 378 compounds of the type (T-2), wherein Y is S, $R^1$ is chlorine, $R^4$ and $R^6$ are methyl, $R^5$ and $R^7$ are hydrogen, and $R^2$ and $R^3$ are as defined in Table 1.

Table 118:
This table covers 378 compounds of the type (T-2), wherein Y is S, $R^1$ is methyl, $R^4$, $R^5$ and $R^6$ are methyl, $R^7$ is hydrogen, and $R^2$ and $R^3$ are as defined in Table 1.

Table 119:
This table covers 378 compounds of the type (T-2), wherein Y is S, $R^1$ is ethyl, $R^4$, $R^5$ and $R^6$ are methyl, $R^7$ is hydrogen, and $R^2$ and $R^3$ are as defined in Table 1.

Table 120:
This table covers 378 compounds of the type (T-2), wherein Y is S, $R^1$ is chlorine, $R^4$, $R^5$ and $R^6$ are methyl, $R^7$ is hydrogen, and $R^2$ and $R^3$ are as defined in Table 1.

Table 121:
This table covers 378 compounds of the type (T-2), wherein Y is S, $R^1$ is methyl, $R^4$, $R^5$, $R^6$ and $R^7$ are methyl, and $R^2$ and $R^3$ are as defined in Table 1.

Table 122:
This table covers 378 compounds of the type (T-2), wherein Y is S, $R^1$ is ethyl, $R^4$, $R^5$, $R^6$ and are methyl, and $R^2$ and $R^3$ are as defined in Table 1.

Table 123:
This table covers 378 compounds of the type (T-2), wherein Y is S, $R^1$ is chlorine, $R^4$, $R^5$, $R^6$ and $R^7$ are methyl, and $R^2$ and $R^3$ are as defined in Table 1.

Table 124:
This table covers 378 compounds of the type (T-2), wherein Y is S=O, $R^1$ is methyl, $R^4$, $R^5$, $R^6$ and $R^7$ are hydrogen, and $R^2$ and $R^3$ are as defined in Table 1.

Table 125:
This table covers 378 compounds of the type (T-2), wherein Y is S=O, $R^1$ is ethyl, $R^4$, $R^5$, $R^6$ and $R^7$ are hydrogen, and $R^2$ and $R^3$ are as defined in Table 1.

Table 126:
This table covers 378 compounds of the type (T-2), wherein Y is S=O, $R^1$ is chlorine, $R^4$, $R^5$, $R^6$ and $R^7$ are hydrogen, and $R^2$ and $R^3$ are as defined in Table 1.

Table 127:
This table covers 378 compounds of the type (T-2), wherein Y is S=O, $R^1$ is methyl, $R^4$ is methyl, $R^5$, $R^6$ and $R^7$ are hydrogen, and $R^2$ and $R^3$ are as defined in Table 1.

Table 128:
This table covers 378 compounds of the type (T-2), wherein Y is S=O, $R^1$ is ethyl, $R^4$ is methyl, $R^5$, $R^6$ and $R^7$ are hydrogen, and $R^2$ and $R^3$ are as defined in Table 1.

Table 129:
This table covers 378 compounds of the type (T-2), wherein Y is S=O, $R^1$ is chlorine, $R^4$ is methyl, $R^5$, $R^6$ and $R^7$ are hydrogen, and $R^2$ and $R^3$ are as defined in Table 1.

Table 130:
This table covers 378 compounds of the type (T-2), wherein Y is S=O, $R^1$ is methyl, $R^4$ and $R^5$ are methyl, $R^6$ and $R^7$ are hydrogen, and $R^2$ and $R^3$ are as defined in Table 1.

Table 131:
This table covers 378 compounds of the type (T-2), wherein Y is S=O, $R^1$ is ethyl, $R^4$ and $R^5$ are methyl, $R^6$ and $R^7$ are hydrogen, and $R^2$ and $R^3$ are as defined in Table 1.

Table 132:
This table covers 378 compounds of the type (T-2), wherein Y is S=O, $R^1$ is chlorine, $R^4$ and $R^5$ are methyl, $R^6$ and $R^7$ are hydrogen, and $R^2$ and $R^3$ are as defined in Table 1.

Table 133:
This table covers 378 compounds of the type (T-2), wherein Y is S=O, $R^1$ is methyl, $R^4$ and $R^6$ are methyl, $R^5$ and $R^7$ are hydrogen, and $R^2$ and $R^3$ are as defined in Table 1.

Table 134:
This table covers 378 compounds of the type (T-2), wherein Y is S=O, $R^1$ is ethyl, $R^4$ and $R^6$ are methyl, $R^5$ and $R^7$ are hydrogen, and $R^2$ and $R^3$ are as defined in Table 1.

Table 135:
This table covers 378 compounds of the type (T-2), wherein Y is S=O, $R^1$ is chlorine, $R^4$ and $R^6$ are methyl, $R^5$ and $R^7$ are hydrogen, and $R^2$ and $R^3$ are as defined in Table 1.

Table 136:
This table covers 378 compounds of the type (T-2), wherein Y is S=O, $R^1$ is methyl, $R^4$, $R^5$ and $R^6$ are methyl, $R^7$ is hydrogen, and $R^2$ and $R^3$ are as defined in Table 1.

Table 137:
This table covers 378 compounds of the type (T-2), wherein Y is S=O, $R^1$ is ethyl, $R^4$, $R^5$ and $R^6$ are methyl, $R^7$ is hydrogen, and $R^2$ and $R^3$ are as defined in Table 1.

Table 138:
This table covers 378 compounds of the type (T-2), wherein Y is S=O, $R^1$ is chlorine, $R^4$, $R^5$ and $R^6$ are methyl, $R^7$ is hydrogen, and $R^2$ and $R^3$ are as defined in Table 1.

Table 139:
This table covers 378 compounds of the type (T-2), wherein Y is S=O, $R^1$ is methyl, $R^4$, $R^5$, $R^6$ and $R^7$ are methyl, and $R^2$ and $R^3$ are as defined in Table 1.

Table 140:
This table covers 378 compounds of the type (T-2), wherein Y is S=O, $R^1$ is ethyl, $R^4$, $R^5$, $R^6$ and $R^7$ are methyl, and $R^2$ and $R^3$ are as defined in Table 1.

Table 141:
This table covers 378 compounds of the type (T-2), wherein Y is S=O, $R^1$ is chlorine, $R^4$, $R^5$, $R^6$ and $R^7$ are methyl, and $R^2$ and $R^3$ are as defined in Table 1.

Table 142:
This table covers 378 compounds of the type (T-2), wherein Y is $S(=O)_2$, $R^1$ is methyl, $R^4$, $R^5$, $R^6$ and $R^7$ are hydrogen, and $R^2$ and $R^3$ are as defined in Table 1.

Table 143:
This table covers 378 compounds of the type (T-2), wherein Y is $S(=O)_2$, $R^1$ is ethyl, $R^4$, $R^5$, $R^6$ and $R^7$ are hydrogen, and $R^2$ and $R^3$ are as defined in Table 1.

Table 144:
This table covers 378 compounds of the type (T-2), wherein Y is $S(=O)_2$, $R^1$ is chlorine, $R^4$, $R^5$, $R^6$ and $R^7$ are hydrogen, and $R^2$ and $R^3$ are as defined in Table 1.

Table 145:
This table covers 378 compounds of the type (T-2), wherein Y is $S(=O)_2$, $R^1$ is methyl, $R^4$ is methyl, $R^5$, $R^6$ and $R^7$ are hydrogen, and $R^2$ and $R^3$ are as defined in Table 1.

Table 146:
This table covers 378 compounds of the type (T-2), wherein Y is $S(=O)_2$, $R^1$ is ethyl, $R^4$ is methyl, $R^5$, $R^6$ and $R^7$ are hydrogen, and $R^2$ and $R^3$ are as defined in Table 1.

Table 147:
This table covers 378 compounds of the type (T-2), wherein Y is $S(=O)_2$, $R^1$ is chlorine, $R^4$ is methyl, $R^5$, $R^6$ and $R^7$ are hydrogen, and $R^2$ and $R^3$ are as defined in Table 1.

Table 148:
This table covers 378 compounds of the type (T-2), wherein Y is $S(=O)_2$, $R^1$ is methyl, $R^4$ and $R^5$ are methyl, $R^6$ and $R^7$ are hydrogen, and $R^2$ and $R^3$ are as defined in Table 1.

Table 149:
This table covers 378 compounds of the type (T-2), wherein Y is $S(=O)_2$, $R^1$ is ethyl, $R^4$ and $R^5$ are methyl, $R^6$ and $R^7$ are hydrogen, and $R^2$ and $R^3$ are as defined in Table 1.

Table 150:
This table covers 378 compounds of the type (T-2), wherein Y is $S(=O)_2$, $R^1$ is chlorine, $R^4$ and $R^5$ are methyl, $R^6$ and $R^7$ are hydrogen, and $R^2$ and $R^3$ are as defined in Table 1.

Table 151:
This table covers 378 compounds of the type (T-2), wherein Y is $S(=O)_2$, $R^1$ is methyl, $R^4$ and $R^6$ are methyl, $R^5$ and $R^7$ are hydrogen, and $R^2$ and $R^3$ are as defined in Table 1.

Table 152:
This table covers 378 compounds of the type (T-2), wherein Y is $S(=O)_2$, $R^1$ is ethyl, $R^4$ and $R^6$ are methyl, $R^5$ and $R^7$ are hydrogen, and $R^2$ and $R^3$ are as defined in Table 1.

Table 153:
This table covers 378 compounds of the type (T-2), wherein Y is $S(=O)_2$, $R^1$ is chlorine, $R^4$ and $R^6$ are methyl, $R^5$ and $R^7$ are hydrogen, and $R^2$ and $R^3$ are as defined in Table 1.

Table 154:
This table covers 378 compounds of the type (T-2), wherein Y is $S(=O)_2$, $R^1$ is methyl, $R^4$, $R^5$ and $R^6$ are methyl, $R^7$ is hydrogen, and $R^2$ and $R^3$ are as defined in Table 1.

Table 155:
This table covers 378 compounds of the type (T-2), wherein Y is $S(=O)_2$, $R^1$ is ethyl, $R^4$, $R^5$ and $R^6$ are methyl, $R^7$ is hydrogen, and $R^2$ and $R^3$ are as defined in Table 1.

Table 156:
This table covers 378 compounds of the type (T-2), wherein Y is $S(=O)_2$, $R^1$ is chlorine, $R^4$, $R^5$ and $R^6$ are methyl, $R^7$ is hydrogen, and $R^2$ and $R^3$ are as defined in Table 1.

Table 157:
This table covers 378 compounds of the type (T-2), wherein Y is $S(=O)_2$, $R^1$ is methyl, $R^4$, $R^5$, $R^6$ and $R^7$ are methyl, and $R^2$ and $R^3$ are as defined in Table 1.

Table 158:
This table covers 378 compounds of the type (T-2), wherein Y is $S(=O)_2$, $R^1$ is ethyl, $R^4$, $R^5$, $R^6$ and $R^7$ are methyl, and $R^2$ and $R^3$ are as defined in Table 1.

Table 159:
This table covers 378 compounds of the type (T-2), wherein Y is $S(=O)_2$, $R^1$ is chlorine, $R^4$, $R^5$, $R^6$ and $R^7$ are methyl, and $R^2$ and $R^3$ are as defined in Table 1.

Table 160:
This table covers 378 compounds of the type (T-2), wherein Y is C=O, $R^1$ is methyl, $R^4$ and $R^5$ are methyl, $R^6$ and $R^7$ are hydrogen, and $R^2$ and $R^3$ are as defined in Table 1.

Table 161:
This table covers 378 compounds of the type (T-2), wherein Y is C=O, $R^1$ is ethyl, $R^4$ and $R^5$ are methyl, $R^6$ and $R^7$ are hydrogen, and $R^2$ and $R^3$ are as defined in Table 1.

Table 162:
This table covers 378 compounds of the type (T-2), wherein Y is C=O, $R^1$ is ethyl, $R^4$ and $R^5$ are methyl, $R^6$ and $R^7$ are hydrogen, and $R^2$ and $R^3$ are as defined in Table 1.

Table 163:
This table covers 378 compounds of the type (T-2), wherein Y is C=O, $R^1$ is methyl, $R^4$, $R^5$ and $R^6$ are methyl, $R^7$ is hydrogen, and $R^2$ and $R^3$ are as defined in Table 1.

Table 164:
This table covers 378 compounds of the type (T-2), wherein Y is C=O, $R^1$ is ethyl, $R^4$, $R^5$ and $R^6$ are methyl, $R^7$ is hydrogen, and $R^2$ and $R^3$ are as defined in Table 1.

Table 165:
This table covers 378 compounds of the type (T-2), wherein Y is C=O, $R^1$ is chlorine, $R^4$, $R^5$ and $R^6$ are methyl, $R^7$ is hydrogen, and $R^2$ and $R^3$ are as defined in Table 1.

Table 166:
This table covers 378 compounds of the type (T-2), wherein Y is C=O, $R^1$ is methyl, $R^4$, $R^5$, $R^6$ and $R^7$ are methyl, and $R^2$ and $R^3$ are as defined in Table 1.

Table 167:
This table covers 378 compounds of the type (T-2), wherein Y is C=O, $R^1$ is ethyl, $R^4$, $R^5$, $R^6$ and $R^7$ are methyl, and $R^2$ and $R^3$ are as defined in Table 1.

Table 168:
This table covers 378 compounds of the type (T-2), wherein Y is C=O, $R^1$ is chlorine, $R^4$, $R^5$, $R^6$ and $R^7$ are methyl, and $R^2$ and $R^3$ are as defined in Table 1.

TABLE 169

This table covers 378 compounds of the type (T-3):

(T-3)

wherein Y is O, $R^1$ is methyl, $R^5$ and $R^6$ are hydrogen, and $R^2$ and $R^3$ are as defined in Table 1.

Table 170
This table covers 378 compounds of the type (T-3), wherein Y is O, $R^1$ is ethyl, $R^5$ and $R^6$ are hydrogen, and $R^2$ and $R^3$ are as defined in Table 1.

Table 171
This table covers 378 compounds of the type (T-3), wherein Y is O, $R^1$ is chlorine, $R^5$ and $R^6$ are hydrogen, and $R^2$ and $R^3$ are as defined in Table 1.

Table 172:
This table covers 378 compounds of the type (T-3), wherein Y is O, $R^1$ is methyl, $R^5$ is hydrogen and $R^6$ is methyl, and $R^2$ and $R^3$ are as defined in Table 1.

Table 173:
This table covers 378 compounds of the type (T-3), wherein Y is O, $R^1$ is ethyl, $R^5$ is hydrogen and $R^6$ is methyl, and $R^2$ and $R^3$ are as defined in Table 1.

Table 174:
This table covers 378 compounds of the type (T-3), wherein Y is O, $R^1$ is chlorine, $R^5$ is hydrogen and $R^6$ is methyl, and $R^2$ and $R^3$ are as defined in Table 1.

Table 175:
This table covers 378 compounds of the type (T-3), wherein Y is O, $R^1$ is methyl, $R^5$ and $R^6$ are methyl, and $R^2$ and $R^3$ are as defined in Table 1.

Table 176:
This table covers 378 compounds of the type (T-3), wherein Y is O, $R^1$ is ethyl, $R^5$ and $R^6$ are methyl, and $R^2$ and $R^3$ are as defined in Table 1.

Table 177:
This table covers 378 compounds of the type (T-3), wherein Y is O, $R^1$ is chlorine, $R^5$ and $R^6$ are methyl, and $R^2$ and $R^3$ are as defined in Table 1.

Table 178:
This table covers 378 compounds of the type (T-3), wherein Y is O, $R^1$ is methyl, $R^5$ is hydrogen and $R^6$ is methoxymethyl, and $R^2$ and $R^3$ are as defined in Table 1.

Table 179:
This table covers 378 compounds of the type (T-3), wherein Y is O, $R^1$ is ethyl, $R^5$ is hydrogen and $R^6$ is methoxymethyl, and $R^2$ and $R^3$ are as defined in Table 1.

Table 180:
This table covers 378 compounds of the type (T-3), wherein Y is O, $R^1$ is chlorine, $R^5$ is hydrogen and $R^6$ is methoxymethyl, and $R^2$ and $R^3$ are as defined in Table 1.

Table 181:
This table covers 378 compounds of the type (T-3), wherein Y is O, $R^1$ is methyl, $R^5$ is hydrogen and $R^6$ is ethoxymethyl, G is hydrogen and $R^2$ and $R^3$ are as defined in Table 1.

Table 182:
This table covers 378 compounds of the type (T-3), wherein Y is O, $R^1$ is ethyl, $R^5$ is hydrogen and $R^6$ is ethoxymethyl, and $R^2$ and $R^3$ are as defined in Table 1.

Table 183:
This table covers 378 compounds of the type (T-3), wherein Y is O, $R^1$ is chlorine, $R^5$ is hydrogen and $R^6$ is ethoxymethyl, and $R^2$ and $R^3$ are as defined in Table 1.

Table 184:
This table covers 378 compounds of the type (T-3), wherein Y is O, $R^1$ is methyl, $R^5$ and $R^6$ are hydrogen, and $R^2$ and $R^3$ are as defined in Table 1.

Table 185:
This table covers 378 compounds of the type (T-3), wherein Y is O, $R^1$ is ethyl, $R^5$ and $R^6$ are hydrogen, and $R^2$ and $R^3$ are as defined in Table 1.

Table 186:
This table covers 378 compounds of the type (T-3), wherein Y is O, $R^1$ is chlorine, $R^5$ and $R^6$ are hydrogen, and $R^2$ and $R^3$ are as defined in Table 1.

Table 187:
This table covers 378 compounds of the type (T-3), wherein Y is O, $R^1$ is methyl, $R^5$ is methyl, $R^6$ is hydrogen, and $R^2$ and $R^3$ are as defined in Table 1.

Table 188:
This table covers 378 compounds of the type (T-3), wherein Y is O, $R^1$ is ethyl, $R^5$ is methyl, $R^6$ is hydrogen, and $R^2$ and $R^3$ are as defined in Table 1.

Table 189:
This table covers 378 compounds of the type (T-3), wherein Y is O, $R^1$ is chlorine, $R^5$ is methyl, $R^6$ is hydrogen, and $R^2$ and $R^3$ are as defined in Table 1.

TABLE 190

This table covers 378 compounds of the type (T-4),

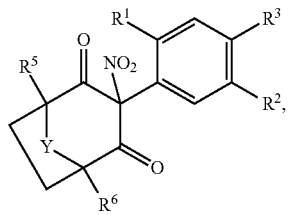
(T-4)

wherein Y is O, $R^1$ is methyl, $R^5$ and $R^6$ are hydrogen, and $R^2$ and $R^3$ are as defined in Table 1.

Table 191
This table covers 378 compounds of the type (T-4), wherein Y is O, $R^1$ is ethyl, $R^5$ and $R^6$ are hydrogen, and $R^2$ and $R^3$ are as defined in Table 1.

Table 192
This table covers 378 compounds of the type (T-4), wherein Y is O, $R^1$ is chlorine, $R^5$ and $R^6$ are hydrogen, and $R^2$ and $R^3$ are as defined in Table 1.

Table 193:
This table covers 378 compounds of the type (T-4), wherein Y is O, $R^1$ is methyl, $R^5$ is hydrogen and $R^6$ is methyl, and $R^2$ and $R^3$ are as defined in Table 1.

Table 194:
This table covers 378 compounds of the type (T-4), wherein Y is O, $R^1$ is ethyl, $R^5$ is hydrogen and $R^6$ is methyl, and $R^2$ and $R^3$ are as defined in Table 1.

Table 195:
This table covers 378 compounds of the type (T-4), wherein Y is O, $R^1$ is chlorine, $R^5$ is hydrogen and $R^6$ is methyl, and $R^2$ and $R^3$ are as defined in Table 1.

Table 196:
This table covers 378 compounds of the type (T-4), wherein Y is O, $R^1$ is methyl, $R^5$ and $R^6$ are methyl, and $R^2$ and $R^3$ are as defined in Table 1.

Table 197:
This table covers 378 compounds of the type (T-4), wherein Y is O, $R^1$ is ethyl, $R^5$ and $R^6$ are methyl, and $R^2$ and $R^3$ are as defined in Table 1.

Table 198:
This table covers 378 compounds of the type (T-4), wherein Y is O, $R^1$ is chlorine, $R^5$ and $R^6$ are methyl, and $R^2$ and $R^3$ are as defined in Table 1.

Table 199:
This table covers 378 compounds of the type (T-4), wherein Y is O, $R^1$ is methyl, $R^5$ is hydrogen and $R^6$ is methoxymethyl, and $R^2$ and $R^3$ are as defined in Table 1.

Table 200:
This table covers 378 compounds of the type (T-4), wherein Y is O, $R^1$ is ethyl, $R^5$ is hydrogen and $R^6$ is methoxymethyl, and $R^2$ and $R^3$ are as defined in Table 1.

Table 201:
This table covers 378 compounds of the type (T-4), wherein Y is O, $R^1$ is chlorine, $R^5$ is hydrogen and $R^6$ is methoxymethyl, and $R^2$ and $R^3$ are as defined in Table 1.

Table 202:
This table covers 378 compounds of the type (T-4), wherein Y is O, $R^1$ is methyl, $R^5$ is hydrogen and $R^6$ is ethoxymethyl, G is hydrogen and $R^2$ and $R^3$ are as defined in Table 1.

Table 203:
This table covers 378 compounds of the type (T-4), wherein Y is O, $R^1$ is ethyl, $R^5$ is hydrogen and $R^6$ is ethoxymethyl, and $R^2$ and $R^3$ are as defined in Table 1.

Table 204:
This table covers 378 compounds of the type (T-4), wherein Y is O, $R^1$ is chlorine, $R^5$ is hydrogen and $R^6$ is ethoxymethyl, and $R^2$ and $R^3$ are as defined in Table 1.

Table 205:
This table covers 378 compounds of the type (T-4), wherein Y is O, $R^1$ is methyl, $R^5$ and $R^6$ are hydrogen, and $R^2$ and $R^3$ are as defined in Table 1.

Table 206:
This table covers 378 compounds of the type (T-4), wherein Y is O, $R^1$ is ethyl, $R^5$ and $R^6$ are hydrogen, and $R^2$ and $R^3$ are as defined in Table 1.

Table 207:
This table covers 378 compounds of the type (T-4), wherein Y is O, $R^1$ is chlorine, $R^5$ and $R^6$ are hydrogen, and $R^2$ and $R^3$ are as defined in Table 1.

Table 208:
This table covers 378 compounds of the type (T-4), wherein Y is O, $R^1$ is methyl, $R^5$ is methyl, $R^6$ is hydrogen, and $R^2$ and $R^3$ are as defined in Table 1.

Table 209:
This table covers 378 compounds of the type (T-4), wherein Y is O, $R^1$ is ethyl, $R^5$ is methyl, $R^6$ is hydrogen, and $R^2$ and $R^3$ are as defined in Table 1.

Table 210:
This table covers 378 compounds of the type (T-4), wherein Y is O, $R^1$ is chlorine, $R^5$ is methyl, $R^6$ is hydrogen, and $R^2$ and $R^3$ are as defined in Table 1.

BIOLOGICAL EXAMPLES

Test Example 1

Monocotyledonous and dicotyledonous test plants were sown in standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants were then grown in a greenhouse under optimum conditions until, 15 days later for post-emergence and 20 days for pre-emergence, the test was evaluated (100=total damage to plant; 0=no damage to plant).

Test Plants:
*Alopecurus myosuroides* (ALOMY), *Avena fatua* (AVEFA), *Lolium perenne* (LOLPE), *Setaria faberi* (SETFA), *Digitaria sanguinalis* (DIGSA), *Echinochloa crus-galli* (ECHCG)

| | | Pre-Emergence Activity | | | | | |
|---|---|---|---|---|---|---|---|
| Compound Number | Rate g/ha | ALOMY | AVEFA | LOLPE | SETFA | DIGSA | ECHCG |
| A1 | 500 | 20 | 30 | 30 | 0 | 70 | 20 |
| A2 | 500 | 0 | 50 | 70 | 90 | 90 | 90 |

| Post-Emergence Activity | | | | | | | |
|---|---|---|---|---|---|---|---|
| Compound Number | Rate g/ha | ALOMY | AVEFA | LOLPE | SETFA | DIGSA | ECHCG |
| A1 | 500 | 60 | 70 | 100 | 100 | 100 | 100 |
| A2 | 500 | 60 | 80 | 100 | 100 | 100 | 100 |

Test Example B

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test Plants:
*Alopecurus myosuroides* (ALOMY), *Avena fatua* (AVEFA), *Setaria faberi* (SETFA), *Echinochloa crus-galli* (ECHCG), *Solanum nigrum* (SOLNI) and *Amaranthus retroflexus* (AMARE)

| Pre-Emergence Activity | | | | | | | |
|---|---|---|---|---|---|---|---|
| Compound Number | Rate g/ha | ALOMY | AVEFA | SETFA | ECHCG | SOLNI | AMARE |
| A4 | 250 | 30 | 70 | 100 | 100 | 0 | 0 |
| A3 | 250 | 0 | 0 | 0 | 50 | 0 | 0 |

| Post-Emergence Activity | | | | | | | |
|---|---|---|---|---|---|---|---|
| Compound Number | Rate g/ha | ALOMY | AVEFA | SETFA | ECHCG | SOLNI | AMARE |
| A4 | 250 | 100 | 90 | 100 | 100 | 0 | 0 |
| A3 | 250 | 0 | 0 | 80 | 80 | 0 | 0 |

What is claimed is:
1. A compound of formula I

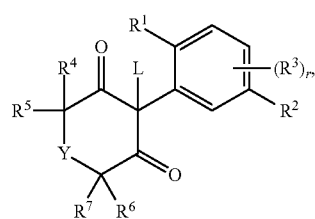

(I)

wherein
$R^1$ is halogen, $C_1$-$C_4$alkyl, $C_1$-$C_4$haloalkyl, $C_3$-$C_6$cycloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, nitro or cyano;

$R^2$ is optionally substituted aryl or optionally substituted heteroaryl;

r is 0, 1, 2 or 3;

$R^3$, if r is 1, is halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylthio, $C_1$-$C_6$alkylsulfinyl, $C_1$-$C_6$alkylsulfonyl, cyano or nitro; or the substituents $R^3$, if r is 2 or 3, independently of each other, are halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylthio, $C_1$-$C_6$alkylsulfinyl, $C_1$-$C_6$alkylsulfonyl, cyano or nitro;

$R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, cyclopropyl or cyclopropyl substituted by $C_1$- or $C_2$alkyl, $C_1$- or $C_2$haloalkyl or halogen; cyclobutyl or cyclobutyl substituted by $C_1$- or $C_2$alkyl; oxetanyl or oxetanyl substituted by $C_1$- or $C_2$alkyl; $C_5$-$C_7$cycloalkyl or $C_5$-$C_7$cycloalkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl or $C_4$-$C_7$cycloalkenyl substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group;

cyclopropyl$C_1$-$C_5$alkyl or cyclopropyl$C_1$-$C_5$alkyl substituted by $C_1$- or $C_2$alkyl, $C_1$- or $C_2$haloalkyl or halogen; cyclobutyl$C_1$-$C_5$alkyl or cyclobutyl$C_1$-$C_5$alkyl substituted by $C_1$-$C_2$alkyl; oxetanyl$C_1$-$C_5$alkyl or oxetanyl$C_1$-$C_5$alkyl substituted by $C_1$- or $C_2$alkyl; $C_5$-$C_7$ cycloalkyl$C_1$-$C_5$alkyl or $C_5$-$C_7$cycloalkyl$C_1$-$C_5$alkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl$C_1$-$C_5$ alkyl or $C_4$-$C_7$cycloalkenyl$C_1$-$C_5$alkyl which is substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; benzyl or benzyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; or $R^4$ and $R^5$, or $R^6$ and $R^7$, are joined to form a 5-7 membered saturated or unsaturated ring in which a methylene group is optionally replaced by an oxygen or sulfur atom, or a 5-7 membered saturated or unsaturated ring substituted by $C_1$- or $C_2$alkyl, where a methylene group of the ring is optionally replaced by an oxygen or sulfur atom; or $R^4$ and $R^7$ are joined to form a 5-7 membered saturated or unsaturated ring unsubstituted or substituted by $C_1$- or $C_2$alkyl, $C_1$- or $C_2$alkoxy, $C_1$-$C_2$alkoxy$C_1$-$C_2$alkyl, hydroxy, halogen, phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl;

Y is O, C=O, $S(O)_m$ or $S(O)_n NR^8$; provided that when Y is C=O, $R^6$ and $R^7$ are different from hydrogen when either $R^4$ or $R^5$ is hydrogen, and $R^4$ and $R^5$ are different from hydrogen when either $R^6$ or $R^7$ is hydrogen;

m is 0 or 1 or 2 and n is 0 or 1;

$R^8$ is hydrogen, $C_1$-$C_6$alkyl, $C_3$-$C_6$cycloalkyl, $C_1$-$C_6$alkoxycarbonyl, tri($C_1$-$C_6$alkyl)silyl-ethyloxycarbonyl, $C_1$-$C_6$haloalkoxycarbonyl, cyano, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkyl-carbonyl, $C_1$-$C_6$cycloalkylcarbonyl, phenylcarbonyl or phenylcarbonyl substituted by $R^9$; benzylcarbonyl or benzylcarbonyl substituted by $R^9$; pyridylcarbonyl or pyridylcarbonyl substituted by $R^9$; phenoxycarbonyl or phenoxycarbonyl substituted by $R^9$; benzyloxycarbonyl or benzyloxycarbonyl substituted by $R^9$;

$R^9$ is $C_1$-$C_6$haloalkyl, $C_1$-$C_6$alkoxycarbonyl, nitro, cyano, formyl, carboxyl or halogen, and L is halogen, nitro, $C_1$-$C_6$alkylthio, thiocyanato or sulfo, and agriculturally acceptable salts thereof.

2. A compound according to claim 1, wherein $R^1$ is halogen, $C_1$-$C_4$alkyl, $C_1$-$C_4$haloalkyl, $C_3$-$C_6$cycloalkyl, $C_2$-$C_4$alkenyl or $C_2$-$C_4$ alkynyl.

3. A compound according to claim 1, wherein $R^2$ is aryl or heteroaryl; or aryl or heteroaryl both substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, phenoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_3$-$C_6$cycloalkyl, $C_1$-$C_4$alkylsulfonyloxy, $C_1$-$C_4$haloalkylsulfonyloxy, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, nitro, cyano, thiocyanato, hydroxy, amino, $C_1$-$C_6$alkylamino, $C_1$-$C_6$dialkylamino, $C_3$-$C_6$cycloalkylamino, morpholino, thiomorpholino, $C_1$-$C_6$alkylcarbonylamino, $C_1$-$C_6$alkoxycarbonylamino, $C_3$-$C_6$ alkenyloxycarbonylamino, $C_3$-$C_6$ alkynyloxycarbonylamino, $C_1$-$C_6$ alkylaminocarbonylamino, di($C_{1-6}$alkyl)aminocarbonylamino, formyl, $C_1$-$C_6$alkylcarbonyl, $C_2$-$C_6$alkenylcarbonyl, $C_2$-$C_6$alkynylcarbonyl, carboxy, $C_1$-$C_6$alkoxycarbonyl, $C_3$-$C_6$alkenyloxycarbonyl, $C_3$-$C_6$alkynyloxycarbonyl, carboxamido, $C_1$-$C_6$alkylaminocarbonyl, di($C_1$-$C_6$alkyl)aminocarbonyl, $C_1$-$C_6$alkylcarbonyloxy, $C_1$-$C_6$alkylaminocarbonyloxy, di($C_1$-$C_6$alkyl)aminocarbonyloxy or $C_1$-$C_6$alkylthiocarbonylamino.

4. A compound according to claim 1, wherein $R^2$ is phenyl or pyridyl or phenyl or pyridyl both substituted by halogen, nitro, cyano, $C_1$-$C_2$alkyl, $C_1$-$C_2$haloalkyl, $C_1$-$C_2$alkoxy or $C_1$-$C_2$haloalkoxy.

5. A compound according to claim 1, wherein $R^3$ is hydrogen, halogen or $C_1$-$C_6$alkyl.

6. A compound according to claim 5, wherein $R^3$ is hydrogen.

7. A compound according to claim 1, wherein $R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$ alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl; $C_5$-$C_7$cycloalkyl or $C_5$-$C_7$cycloalkyl substituted by $C_1$- or $C_2$alkyl or $C_1$- or $C_2$haloalkyl and in which a methylene group is optionally replaced by an oxygen or sulfur atom or a sulfinyl or sulfonyl group; $C_5$-$C_7$cycloalkyl$C_1$-$C_5$alkyl or $C_5$-$C_7$cycloalkyl$C_1$-$C_5$alkyl substituted by $C_1$-$C_2$alkyl or $C_1$- or $C_2$haloalkyl and in which a methylene group is optionally replaced by an oxygen or sulfur atom or a sulfinyl or sulfonyl group.

8. A compound according to claim 7, wherein, $R^4$, $R^5$, $R^6$ and $R^7$, independently of each other, are hydrogen, $C_1$-$C_2$alkyl, $C_1$-$C_2$haloalkyl or $C_1$-$C_2$alkoxy$C_1$-$C_2$alkyl.

9. A compound according to claim 8, wherein Y is O.

10. A process for the preparation of a compound of the formula I, which comprises reacting the compound of the formula

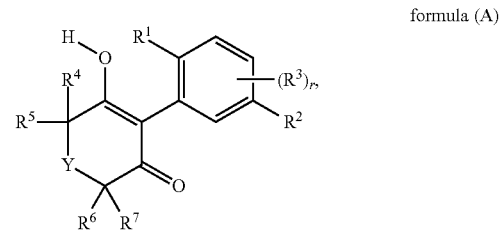

formula (A)

wherein $R^1$, $R^2$, $R^3$, $R^4$, $R^5$, $R^6$ and $R^7$, Y and r are as defined in claim 1, with a halogenating agent selected from the group consisting of chlorine, N-chlorosuccinimide, sulfuryl chloride, bromine and N-bromosuccinimide in the presence of a solvent selected from dichloromethane and chloroform.

11. A process for the preparation of compounds of the formula I, which comprises reacting the compound of the formula

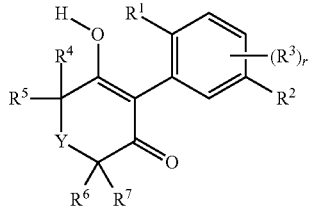

formula (A)

wherein $R^1$, $R^2$, $R^3$, $R^4$, $R^5$, $R^6$ and $R^7$, Y and r are as defined in claim 1, with a nitrating agent, in the presence of a solvent, wherein the nitrating agent comprises sodium nitrite and fuming nitric acid, and the solvent is glacial acetic acid.

12. A method of controlling grasses and weeds in crops of useful plants, which comprises applying a herbicidally effective amount of a compound of formula I, or of a composition comprising such a compound, to the plants or to the locus thereof.

13. A herbicidal composition, which, in addition to comprising at least one formulation adjuvant, comprises a herbicidally effective amount of a compound of formula I.

14. A composition according to claim 13, which, in addition to comprising the compound of formula I, comprises a further herbicide as mixing partner, and optionally a safener.

15. A compound according to claim 1, wherein $R^1$ is $C_1$-$C_4$alkyl, $R^2$ is phenyl or phenyl substituted by halogen or $C_1$-$C_2$alkyl, $R^3$ is hydrogen, $R^4$, $R^5$, $R^6$ and $R^7$, independently of each other are $C_1$-$C_2$alkyl, Y is O, and L is chloro or nitro.

* * * * *